(12) United States Patent
Prevost

(10) Patent No.: US 12,296,736 B2
(45) Date of Patent: May 13, 2025

(54) MOBILE UNIT FOR THOROUGH WET DECONTAMINATION OF PERSONS

(71) Applicant: UTILIS, Ennery (FR)

(72) Inventor: Philippe Prevost, Metz (FR)

(73) Assignee: Utilis, Ennery (FR)

( * ) Notice: Subject to any disclaimer, the term of this patent is extended or adjusted under 35 U.S.C. 154(b) by 185 days.

(21) Appl. No.: 17/596,801

(22) PCT Filed: Jun. 16, 2020

(86) PCT No.: PCT/IB2020/055609
§ 371 (c)(1),
(2) Date: Dec. 17, 2021

(87) PCT Pub. No.: WO2020/254955
PCT Pub. Date: Dec. 24, 2020

(65) Prior Publication Data
US 2022/0314863 A1   Oct. 6, 2022

(30) Foreign Application Priority Data
Jun. 21, 2019   (FR) ...................................... 1906703

(51) Int. Cl.
*B60P 3/00* (2006.01)
*E04H 1/12* (2006.01)

(52) U.S. Cl.
CPC ............ *B60P 3/005* (2013.01); *E04H 1/1277* (2013.01)

(58) Field of Classification Search
CPC .. A47K 3/286; A61G 13/0027; A61G 7/0005; A61G 3/0218–068; A61G 1/003; A61G 1/06; B60P 3/005; E04H 1/1277
(Continued)

(56) References Cited

U.S. PATENT DOCUMENTS

| 4,348,777 A | * | 9/1982 | Peterson | ................ A47K 3/286 4/596 |
| 4,796,311 A | * | 1/1989 | Shankman | ............ E04H 1/1277 4/596 |

(Continued)

FOREIGN PATENT DOCUMENTS

| DE | 4007740 | * | 9/1991 | ........... E04H 1/1277 |
| DE | 19814740 | * | 10/1999 | ............. B60P 3/005 |
| WO | 2007144490 A1 | | 12/2007 | |

*Primary Examiner* — David P Angwin
*Assistant Examiner* — Nicholas A Ros
(74) *Attorney, Agent, or Firm* — Colson Law Group, PLLC

(57) ABSTRACT

The invention relates to a mobile decontamination unit for thorough wet decontamination of persons, having a generally rectangular parallelepiped shape with a longitudinal axis and a transverse axis. The unit comprises a technical module and at least one shower module, which are adjacent to one another in the direction of the longitudinal axis. The unit also comprises a first retractable extension of the shower module in the direction of the transverse axis, on one side of said shower module, and/or a second retractable extension of the shower module in said direction of the transverse axis, on the other side of said shower module. The shower module and the one or more extensions comprise a decontamination line for persons for the circulation, in the direction of the transverse axis, of persons to be decontaminated by showering in the shower module.

15 Claims, 15 Drawing Sheets

(58) Field of Classification Search
USPC .............................................................. 4/900
See application file for complete search history.

(56) References Cited

U.S. PATENT DOCUMENTS

| | | | | | |
|---|---|---|---|---|---|
| 5,178,432 | A | * | 1/1993 | Zeman | A61G 3/0833 |
| | | | | | 296/25 |
| 5,551,102 | A | * | 9/1996 | Stewart | E04H 1/1277 |
| | | | | | 4/612 |
| 5,779,296 | A | * | 7/1998 | Hewko | A61G 3/0866 |
| | | | | | 244/118.6 |
| 6,842,923 | B1 | * | 1/2005 | Castellani | A61G 1/013 |
| | | | | | 16/374 |
| 6,966,900 | B1 | * | 11/2005 | Chyba | A61H 33/00 |
| | | | | | 604/290 |
| 2003/0037812 | A1 | | 2/2003 | Stewart et al. | |
| 2004/0238007 | A1 | * | 12/2004 | Jones | A61L 2/18 |
| | | | | | 134/32 |
| 2005/0053533 | A1 | * | 3/2005 | Brown | E04H 1/1277 |
| | | | | | 422/255 |
| 2010/0299826 | A1 | * | 12/2010 | Grcevic | E04B 1/3431 |
| | | | | | 4/599 |
| 2010/0304658 | A1 | * | 12/2010 | Grcevic | B60P 3/14 |
| | | | | | 454/187 |
| 2013/0227790 | A1 | * | 9/2013 | Kostron | A61G 1/048 |
| | | | | | 5/628 |
| 2018/0271723 | A1 | * | 9/2018 | Adkins | A61G 1/048 |

* cited by examiner

Fig. 13
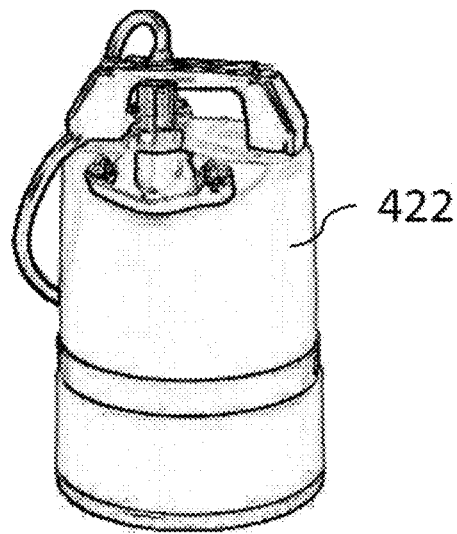
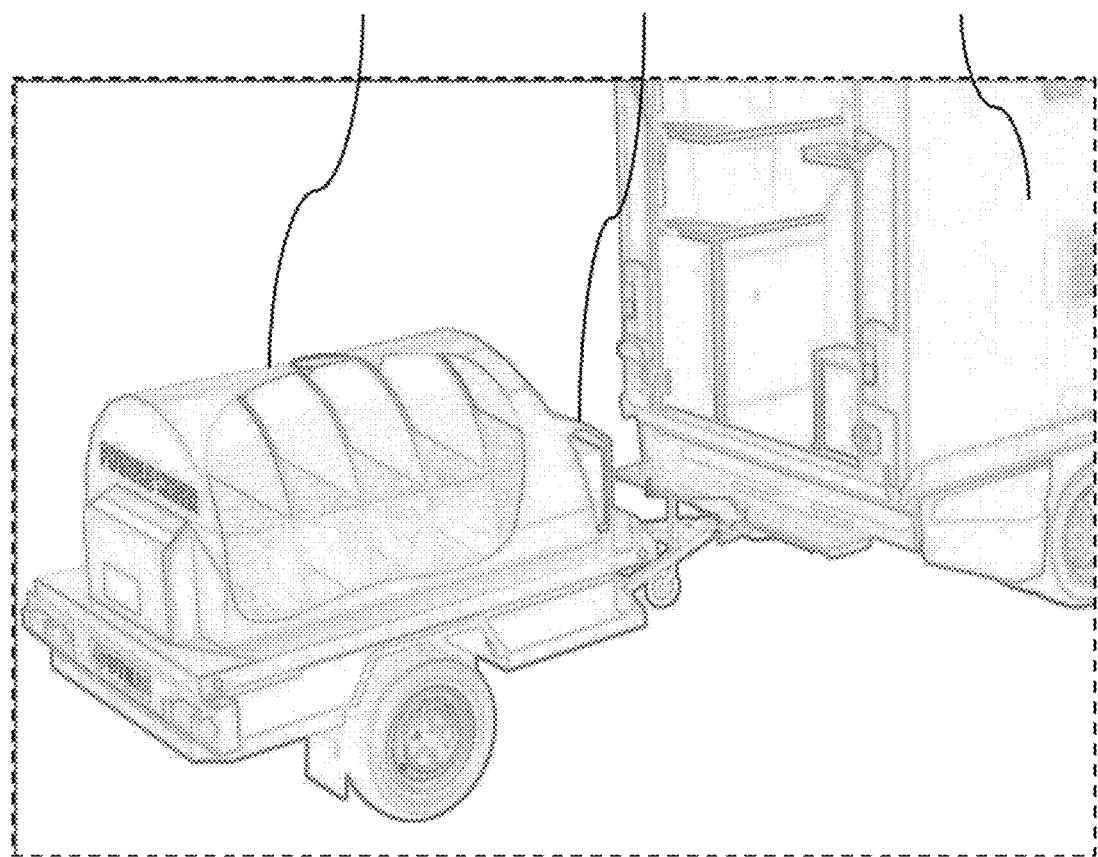
Fig. 14

MOBILE UNIT FOR THOROUGH WET DECONTAMINATION OF PERSONS

TECHNICAL FIELD

The present invention relates generally to the decontamination of persons, for example following an incident whereby a hazardous material is transferred from its source to persons. More specifically it relates to a mobile decontamination unit (MDU), for the thorough wet decontamination of persons.

PRIOR ART

Decontamination of persons means a physical and/or chemical method for reducing, or eliminating, and preventing the spread of contamination to persons. Concerning the risk of dispersal, it is known that people, animals, the environment or equipment can serve as vectors for the transmission of contamination, which is why it is desirable to decontaminate people who have been contaminated or simply exposed to a risk of contamination. Decontamination may be performed at the site of an incident involving a contaminant. It may also be carried out at the hospital entrance when evacuations of people from the accident site to a hospital have taken place in an uncontrolled manner.

In the context of the invention, a contaminating agent or product (also called "contaminant" for short) refers to any hazardous material with a low volatility, persistence and toxicity in small quantities, which is physically and/or chemically remains on people, and which is likely to generate intoxication in case of exposure.

Decontamination in the context of NRBC (nuclear, radiological, biological or chemical), for example, begins with screening the population concerned. This separates, where appropriate, asymptomatic (As), symptomatically able-bodied (AB), and symptomatically disabled (SD) persons.

A primary decontamination, or emergency decontamination, is then carried out, followed possibly, but not always, by the implementation of a secondary decontamination, or thorough decontamination, allowing a fine decontamination within the context of a decontamination chain.

The objectives of emergency decontamination are to reduce contamination on the victims and to limit, as much as possible, the transfer of liquid and/or solid agents, which may be volatile, onto emergency personnel and equipment. This procedure is also intended to reduce the risk of poisoning through desorption of contaminants from clothing. It is broken down as follows:
  dry decontamination: ab (ad) sorption and displacement of toxic agents present on the body surface (using Fuller's earth or other absorbent products such as absorbent cloth/paper, etc.);
  the removal of at least the superficial (outer) layers of clothing and footwear; and,
  dressing with a kit (e.g., pajamas or equivalent) if the victim is referred to the reception center for those involved (i.e., CADI) or with a survival blanket if referred to a thorough decontamination (see infra).

In a difficult situation, depending on the resources available, it is possible to proceed, after undressing, with decontamination by transfer using the mechanical effect of water, either by means of a hydraulic tunnel (fire engine tunnel providing a water deluge) or with showers in whatever infrastructure is available in the immediate vicinity (gymnasium, swimming pool, etc.).

In-depth decontamination (or "wet" decontamination) aims to eliminate the contaminants still present on the body surface that can be moved off by the mechanical action of water. To this end, it is broken down as follows:
  complete disrobing of the victims;
  washing by showering with water containing a liquid soap surfactant, such as liquid surgical soap (about 0.5%), for a specific period of time, about 2 minutes; and,
  rinsing by showering with clear water for a set period of time, about 2 minutes as for washing.

People with long hair can take two shower cycles. Washing can be optimized with a single-use washcloth. Thus, the care of victims after decontamination (treatment, evacuation) can be done without specific protective equipment. It should be noted that thorough decontamination is not always performed. After an initial phase of uncertainty, it may be called into question depending on the exposure context (case of highly volatile gases or agents, etc.).

Emergency decontamination is most effective when it is performed as soon as possible after exposure to the toxic agents. This implies that it should ideally be carried out as an emergency, directly at the site of contamination where bodies have been exposed to contaminants. This is why emergency services, such as the fire brigade, or the military, which can sometimes be called upon even in the event of a purely civil disaster such as an industrial accident, have mobile equipment to carry out emergency decontamination operations. Such mobile equipment can be quickly projected to the scene of the disaster.

Conversely, the thorough decontamination equipment is a fixed facility permanently positioned in predetermined locations, particularly at potentially hazardous sites. Their location is defined according to information collected prior to any contamination event, as part of a risk analysis, for example an industrial risk analysis. As a result, in the event of a disaster, the facility may be too close or too far from the place of need. The invention has applications, in particular, in the thorough wet decontamination of able-bodied or disabled victims. More particularly, the invention aims at providing a mobile unit for the thorough decontamination of persons. As it is mobile, contrary to prior art deep decontamination facilities, it can be moved after the occurrence of a contaminating event in order to be used as close as possible to the contaminated area. The unit therefore allows the wet decontamination medium to be positioned immediately and at the exact location required. In this context, the person skilled in the art will appreciate that the proposed mobile deep decontamination unit allows for thorough wet decontamination, whereas the state of the art only allows for emergency decontamination, which is generally carried out as dry only decontamination, except for the possibility of using a fire engine tunnel ensuring a water deluge or showers in infrastructure available in the immediate vicinity, as described above.

Wet decontamination refers to any decontamination technique that dissolves the contaminant and transfers it from the carrier to the effluents. Decontamination by washing or showering with water alone, for example, is already an excellent method of mass decontamination. Washing with water and a dissolving agent (such as 0.5% surgical soap), followed by rinsing the victims' bodies, improves the removal of the contaminant. But this increases the length of the decontamination process for each victim. Wet decontamination is a time-consuming, and labor-intensive process.

However, the material and human resources available are usually very limited. Performing rescue and recovery procedures, then the first medical treatment, followed by triaging able-bodied and disabled victims, and then evacuating them to the hospital, are all operations that require the material and human resources of the rescue forces.

In addition, the site of the incident that caused the contamination quickly becomes the scene of intense activity after the arrival of the rescue forces, due to the multitude of operations mentioned above that must be carried out simultaneously and urgently. The management of space and the flow of people very quickly become issues of primary importance for the overall effectiveness of the rescue effort, especially when the number of victims is high.

For all these reasons, there is a need for a mobile decontamination unit for the wet decontamination of persons, which can ensure a high throughput of decontaminated persons, and which structures and streamlines the flow of people in the vicinity of the decontamination unit in order to minimize the impact of decontamination operations on the efficiency of other operations (rescue operations, medical care, triaging able-bodied and disabled victims, and evacuating victims, in particular).

SUMMARY OF THE INVENTION

The invention aims to eliminate, or at least mitigate, all or at least some of the aforementioned drawbacks.

To this end, a first aspect of the invention proposes a mobile decontamination unit for wet decontamination of persons, having the general shape of a rectangular parallelepiped with a longitudinal axis and a transverse axis, characterized in that it comprises:

a technical module and at least one shower module, which are adjacent to each other in the direction of the longitudinal axis;

a first extension of the shower module, which can be retracted in the direction of the transverse axis, on one side of the shower module and/or a second extension of the shower module, which can be retracted in the direction of the transverse axis, on the other side of the shower module, wherein the shower module and the first and/or second extension thereof comprise at least one person-decontamination line for the circulation of persons to be decontaminated by showering in the shower module in the direction of the transverse axis.

In one embodiment, the shower module as well as its first extension and/or its second extension comprise at least two able-bodied victim decontamination lines, which are adapted to be operated in parallel with common technical means comprised in the technical module.

In one embodiment, the decontamination lines can be adapted to be operated in parallel but independently of each other.

In one embodiment, the shower module may comprise a removable wall extending in the direction of the transverse axis to separate two shower compartments of the shower module, said shower compartments belonging to the first decontamination line and the second decontamination line, respectively, and the first extension and/or the second extension of the shower module may then each comprise a wall extending in the direction of the transverse axis to separate said extension into two compartments, said compartments belonging to the first decontamination line and the second decontamination line, respectively.

In one embodiment, the first and second extensions of the shower module form a person undressing compartment and a person re-dressing compartment, respectively.

In one embodiment, the shower module may be equipped with a decontamination shower and a rinsing shower for each decontamination line, each comprising a shower head with a supply circuit fed with a decontamination solution and with another supply circuit fed with clean water, respectively.

The decontamination unit may comprise a single buffer tank which is located under a grated floor of the shower module, and may further comprise a pump which is located in the engineering module and is adapted to draw waste water into the buffer tank and discharge it to one or more flexible waste water collection tanks which may be located outside the decontamination unit.

In one embodiment, the bottom of the buffer tank may have a V-shaped profile, with a slope directed towards the pump.

In one embodiment, the first extension and/or the second extension of the shower module are made of canvas, and are unfoldable and collapsible with frame elements and posts from which the canvas is supported, said canvas, frame elements, and posts being retractable into the wall of the shower module.

In one embodiment, the technical module may further comprise a fan connected to an air diffusion duct opening into the second extension, and adapted to provide an air flow ensuring a sweep of overpressure air from the second extension to the first extension through the shower module.

In one embodiment, the operation of the shower module of the unit may be automatic, and timed by light indicators placed above the entrance door, the exit door and in the middle of the two shower compartments, with the light turning red or green depending on the operation of the showers.

In one embodiment, the shower module, as well as its first extension and/or its second extension, may comprise at least one disabled victim decontamination line, which is adapted to be operated, in a fallback mode, as an able-bodied person decontamination line.

In one embodiment, the disabled decontamination line comprises:

high supports with stretcher rails arranged in the first and second extension;

a lifting table with two low and high positions, arranged in the shower module, the low position of the lifting table being flush with the stretcher rails of the first extension and with the stretcher rails of the second extension, the lifting table being operatively aligned with said stretcher rails so as to form a stretcher line in the direction of the transverse axis Y.

In one embodiment, the decontamination unit comprises at least one stretcher for carrying a disabled person along the disabled decontamination line, the canvas of which is perforated so that water can flow through.

In a second aspect, the invention also relates to a method of operating a decontamination unit according to one of the above first aspects, wherein the operation of showers of the shower module is automatic, and is controlled in rhythm with the illumination of light indicators adapted to signal to able-bodied persons their progress through the able-bodied person decontamination line.

BRIEF DESCRIPTION OF THE FIGURES

Further features and advantages of the invention will become apparent from the following description. This is purely illustrative and should be read in conjunction with the attached drawings in which:

FIG. 13 is a view of a pump forming part of the waste water discharge means of FIG. 12;

FIG. 14 is a view of a clean water tank of the decontamination unit;

DESCRIPTION OF EMBODIMENTS

Figure 1:
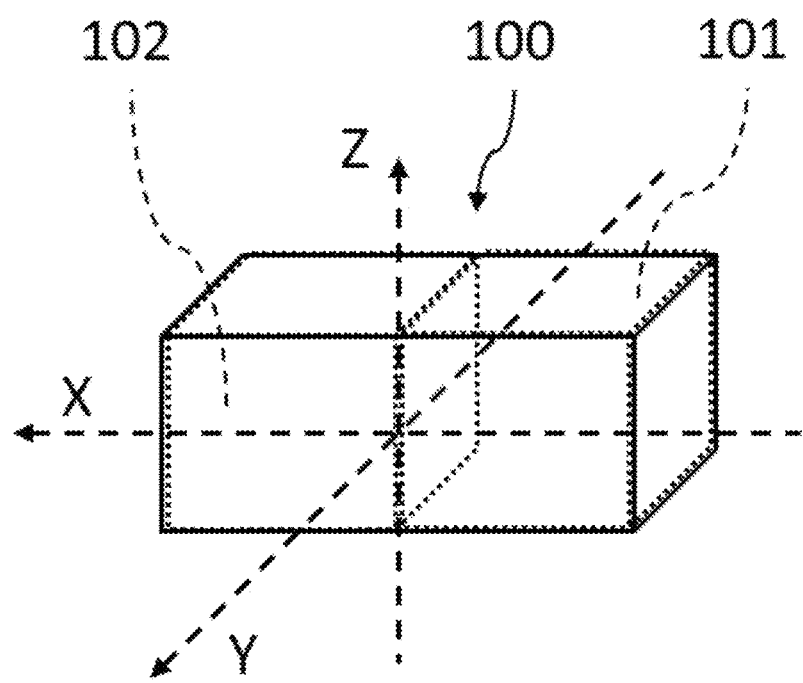
FIG. 1 is a schematic representation of the general shape of the decontamination unit according to embodiments.

In the following description of embodiments and in the Figures of the attached drawings, the same or similar elements bear the same numerical references as in the drawings.

With reference to FIG. 1, a mobile decontamination unit according to the embodiments is a cell 100 which has the general shape of a rectangular parallelepiped, with a longitudinal axis X, a transverse axis Y, and a vertical axis Z. A rectangular parallelepiped is a solid figure bounded by six rectangular faces (rectangular box), all of whose angles are right angles and whose opposite faces are equal.

In practice, the cell 100 may be fixedly or transferably mounted on the chassis of a carrier vehicle.

Figure 2:
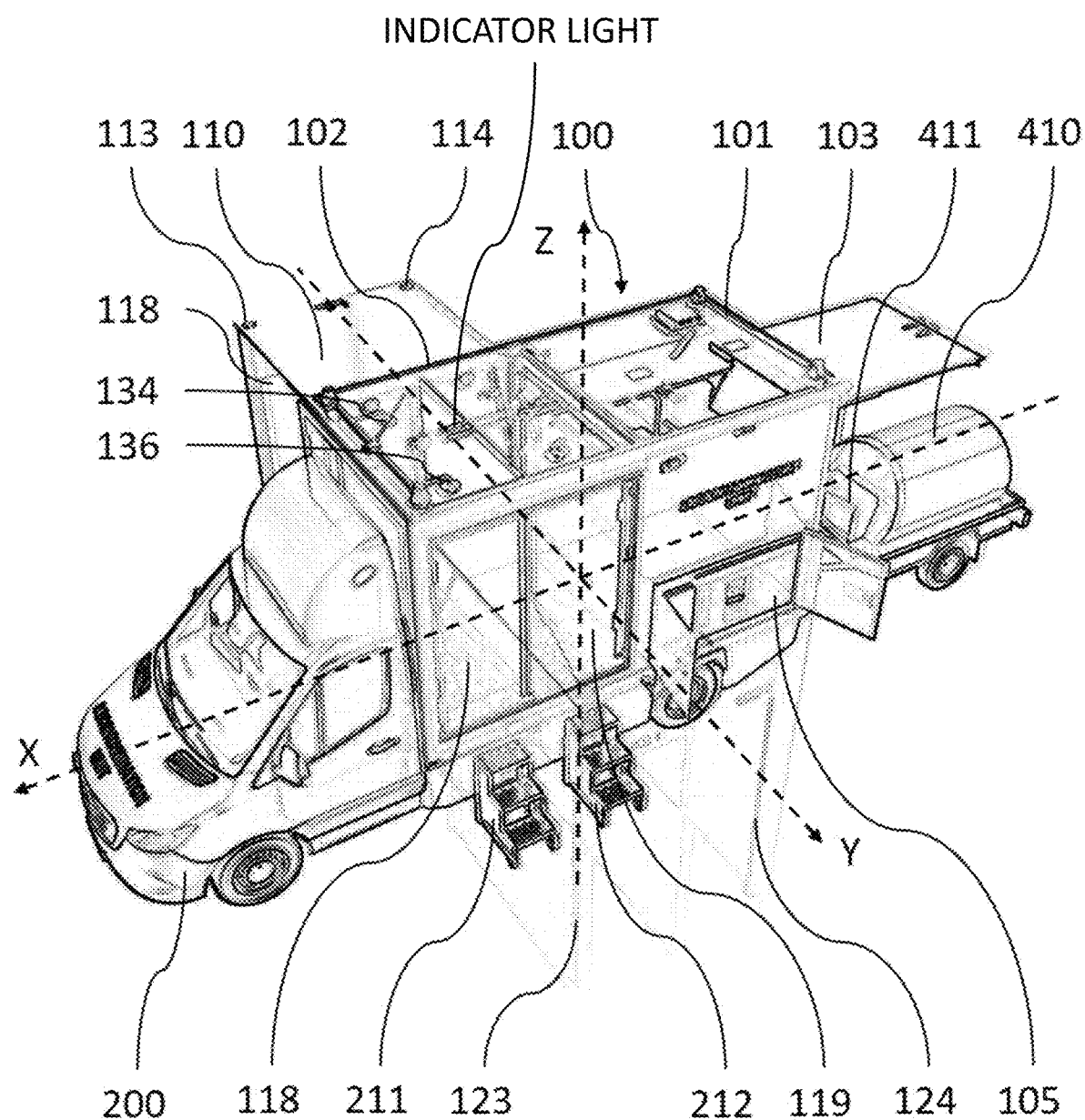
FIG. 2 is a three-dimensional view of the decontamination unit mounted on a carrier vehicle, according to a version of the decontamination unit equipped with a shower module adapted for disabled persons.
Figure 3:
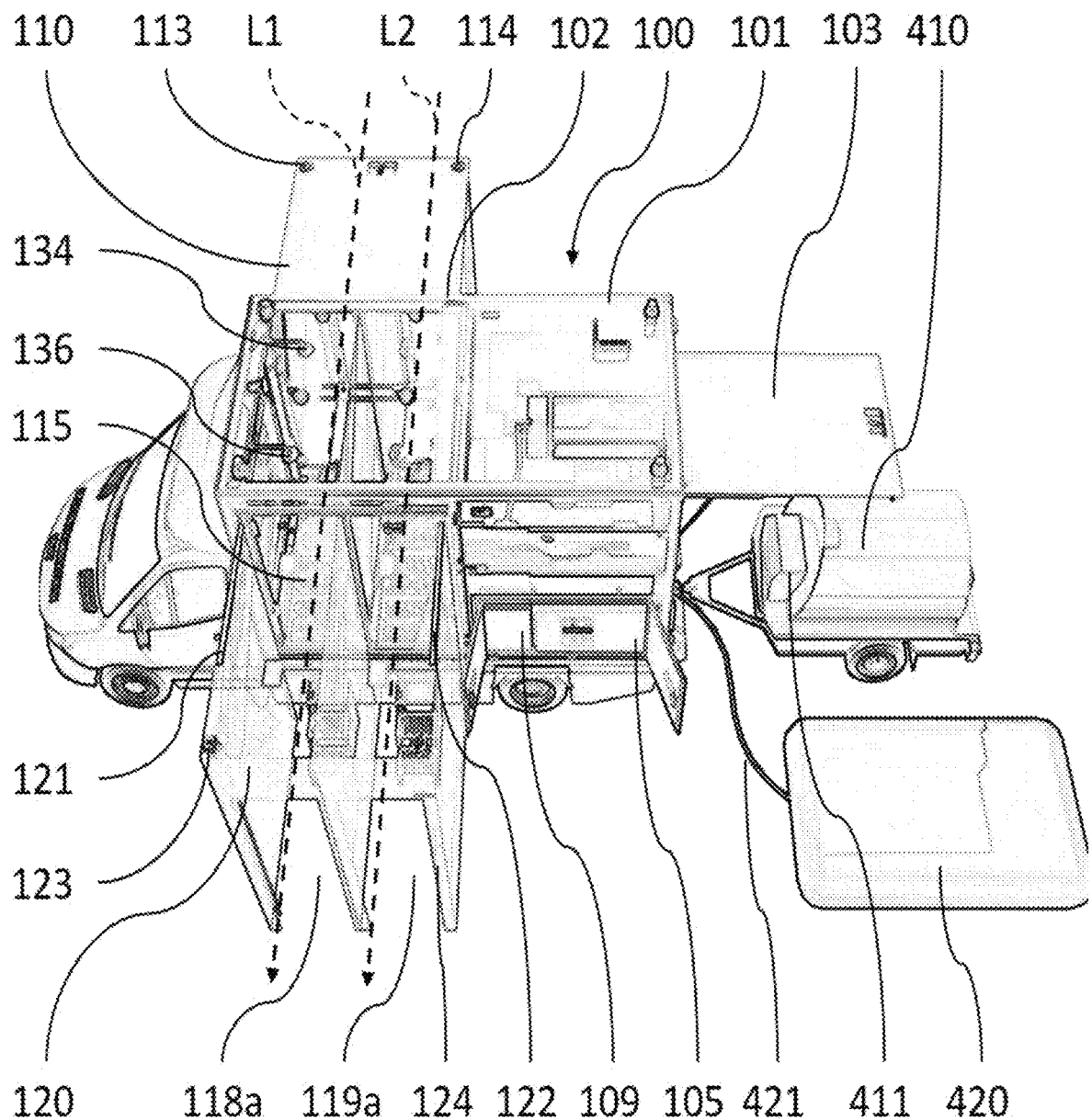
FIG. 3 is another view of the decontamination unit of FIG. 1.

In the non-limiting case of the embodiments envisaged in the present description and represented in particular in FIG. 2 and FIG. 3, such a carrier vehicle 200 is, for example, a carrier chassis of the flatbed truck type of the MERCEDES® brand. More specifically, it may be a SPRINTER® 519 CDi type vehicle, in a 5-ton heavy-duty version, equipped for example with a 190 HP 6-cylinder engine with 2987 cc of displacement and a torque of 440 Nm at 1400-2400 rpm, as well as an automatic gearbox.

In such an installation, the longitudinal axis X of the cell 100 coincides with the longitudinal axis of the carrier vehicle 200, and is oriented towards the front of said vehicle with reference to the direction of travel of the vehicle in normal or forward motion. Therefore, by convention and unless expressly stated otherwise, the terms "front" and "rear" and their derivatives "frontward" and "rearward", or "forward" and "rearward", as well as the terms "ahead" and "behind", are used in the following with reference to the direction of the longitudinal axis X of the carrier vehicle 200, oriented in the forward direction of the vehicle.

Furthermore, the transverse axis Y of the cell 100 coincides with the longitudinal axis of the carrier vehicle 200. The terms "side" and "lateral" and their derivatives, and the terms "left" and "right" and their derivatives "left-hand" and "right-hand", or "leftward" and "rightward", are used in the following with reference to the direction of the transverse axis of the carrier vehicle 200 and from the perspective of an observer facing in the forward direction of the vehicle.

Finally, the person skilled in the art will appreciate that the direction of the vertical axis Z of the cell 100 or carrier vehicle 200 corresponds to the direction of gravity. Therefore, unless expressly stated otherwise, the terms "top" and "bottom" and their derivatives "up" and "down", or "upward" and "downward", as well as the terms "upper" and "lower" and the terms "above" and "below" and their derivatives "atop" or "beneath" and "over" or "under", are used in the following with reference to the direction of the vertical Z axis.

Still referring to FIG. 1, and as shown in particular in FIGS. 2 and 3, the cell 100 of the decontamination unit according to embodiments comprises two modules 101 and 102, adjacent to each other in the direction of the longitudinal axis X. Module 101 is a technical module, and module 102 is a shower module adapted for wet decontamination of persons.

The technical module 101 groups together all the equipment and control elements necessary for the operation of the decontamination unit 100. In the example shown, the technical module 101 is located at the rear of the cell 100. In such a case, it is advantageously accessed from the rear of the vehicle 200, via a rear door 103, for example a tailgate opening upwards. As will become apparent in the remainder of this discussion, access to the technical module 101 by an operator 300 can thus be made without mutual interference with the circulation of persons in the decontamination line(s) L1 and L2, or L3, which pass transversely through the shower module 102.

Due to the design and arrangement of the shower module 102 at the front of the vehicle 200, for example just behind the vehicle cab, the entire exterior area at the rear of the vehicle 200 is effectively free of any circulation of persons to be decontaminated. This area can be organized by the rescue forces when the decontamination unit is deployed, with access reserved for the operators of the decontamination unit to allow them to perform technical operations. These operations include, for example, the filling or replacement of a trailer of the truck 200 comprising a tank 410 which is connected to the technical module 101, and/or the installation and removal and/or replacement of a wastewater collection reservoir 420 which is also connected to the technical module 101. This tank 410 and this reservoir 420 are in fact coupled to the technical module 101 to allow its operational functioning, so that the aforementioned operations are facilitated by the fact that said module is at the rear of the vehicle 200. These operations typically require another vehicle to approach, for example, to drop off an operator closer to the technical module to reduce exposure to potential ambient contaminant fallout at the work site, and/or to remove the tank 410 when it is empty, and/or to drop off a replacement tank when it is full, or to remove the wastewater reservoir 420 when it is full and drop off another reservoir in its place. It is therefore advantageous that the tank 410 and the reservoir 420 can be arranged in the area at the rear of the vehicle 200 and the technical module 110, which itself is arranged at the rear of the vehicle for this purpose and for the effect of access by operators from the rear of the vehicle 200, while the movement of persons through the shower module 102 is transversely from one side to the other of the decontamination unit 100 and thus of the vehicle 200.

As you can see, the flow of persons to be decontaminated does not pass through the area behind unit 100 and therefore the carrier truck 200, so there is no mutual interference. The circulation of the persons to be decontaminated is thus fluid and fast, and the operations of access to the technical module 101 by the operator and/or the operations in relation to the equipment connected to it such as the tank 410 and the reservoir 420 are made easier because the other vehicles and/or the operators involved in these operations can approach the decontamination unit 100 without posing a risk to or interfering with said persons.

Another advantage of the arrangement of the technical module 101 at the rear of the cell 100 and thus of the vehicle 200, is that the tailgate 103 also makes it possible, when it is in the raised position, to protect the operator 300 and the equipment that they are using from the rain and from possible fallout of contaminating products floating in the ambient space, when the operator 300 descends from said technical module 101 to service the tank 4410 and/or the reservoir 420.

The decontamination lines L1 and L2 (in the case of the able-bodied person decontamination unit according to the embodiments shown in FIGS. 6, 7 and 8), or the decontamination line L3 (in the case of the disabled person decontamination unit according to the embodiments shown in FIGS. 6, 7 and 8), will now be described in general terms. Briefly, the decontamination lines followed by the persons to be decontaminated extend transversely to the unit 100 in the Y-axis direction. Persons enter and exit the shower module 102 through side doors of the shower module 102 provided on the left and right sides of the shower module, respectively.

In the example of an able-bodied person decontamination unit shown in FIGS. 2, 3, 6, 7 and 8, the unit 100 comprises two decontamination lines L1 and L2, which are adapted to be operated in parallel to each other. These lines L1 and L2 run parallel to each other in the transverse direction Y. The shower module 102 thus comprises two shower compartments, namely one such compartment for each of the decontamination lines L1 and L2, respectively.

The interior dimensions of a compartment of the shower module 102 are, for example, 2000×900 mm, i.e. 2000 mm long (in the transverse direction Y of the unit 100 and the vehicle 200, between the right side and the left side of said vehicle), by 900 mm wide (in the longitudinal direction X of the unit 100).

Figure 7:
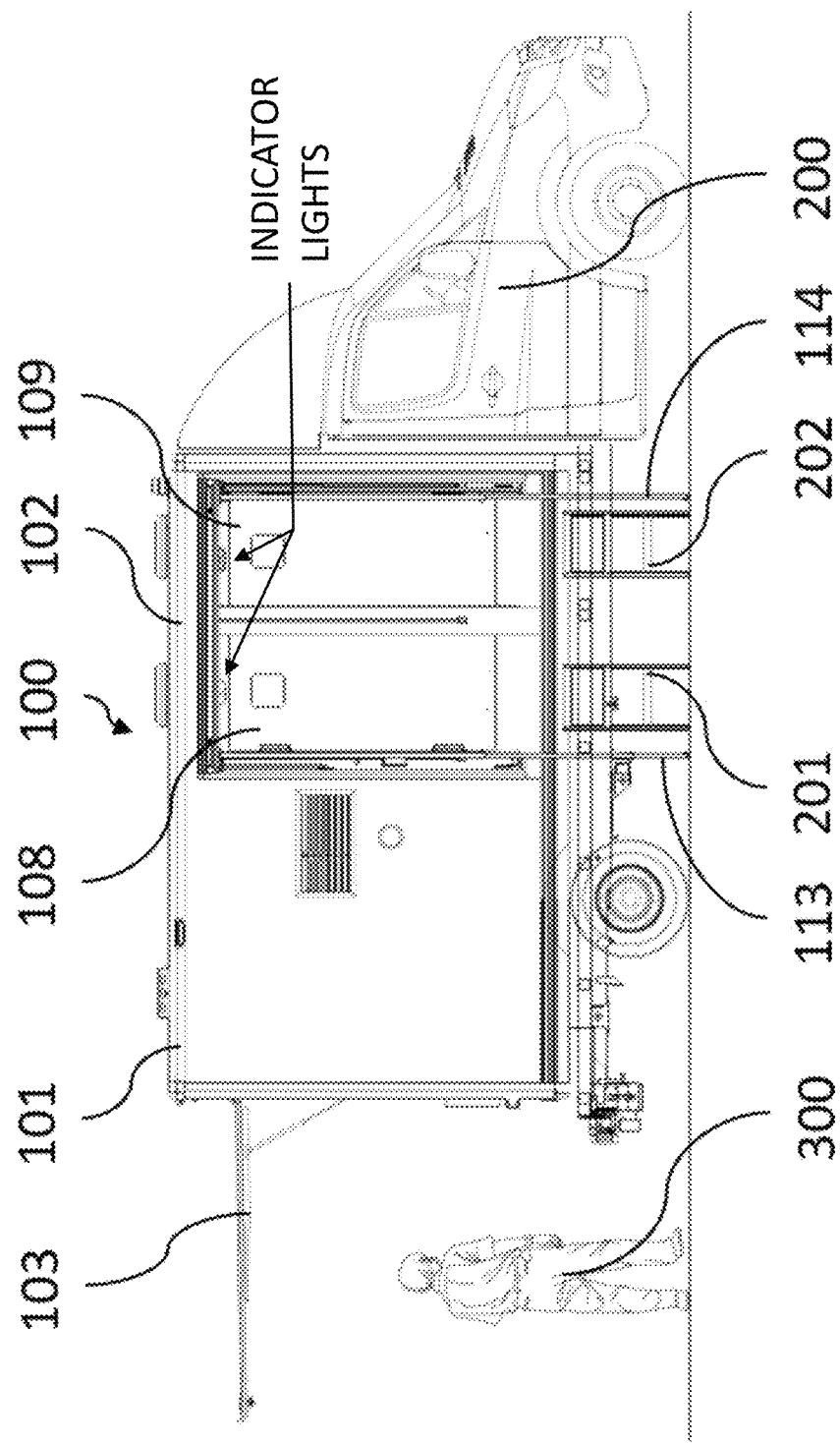
FIG. 7 is a right side view of the able-bodied person decontamination unit of FIGS. 2 and 3.
Figure 8:
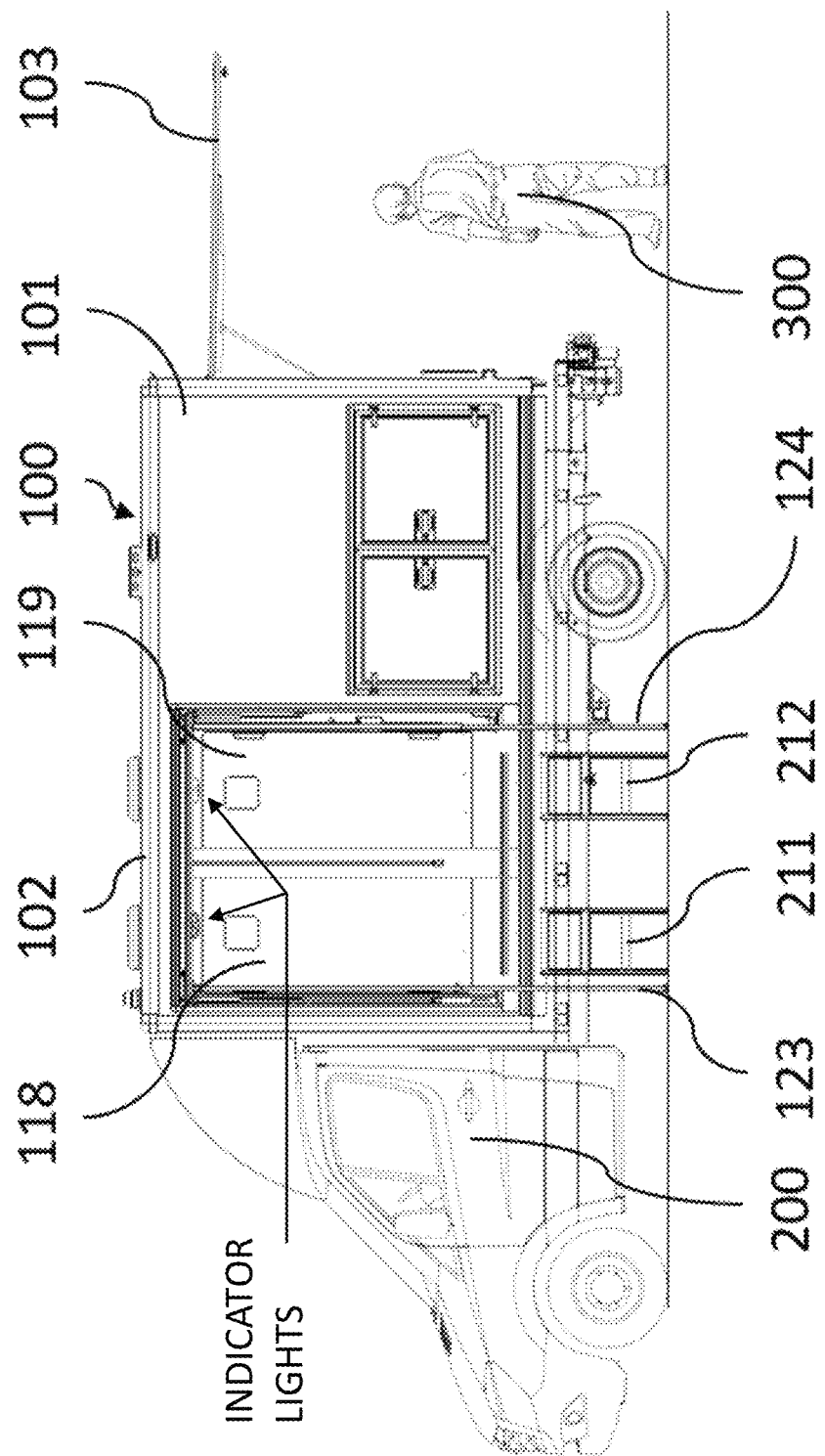
FIG. 8 is a left side view of the able-bodied person decontamination unit of FIGS. 2 and 3.

With particular reference to FIGS. 7 and 8, entry to and exit from the shower compartment 102 is via rigid doors of said compartment 102. These doors are referenced 108 and 109 in FIG. 7 for the entrance doors of each of the decontamination lines L1 and L2, located on the right side of the unit 102. The exit doors of each of the decontamination lines L1 and L2, located on the right side of the unit 102 are referenced 118 and 119 in FIG. 8. The rigid doors 108, 109, 118 and 119 are, for example, made of compact laminate material. A door made of such an inert material has the advantage that it does not react with temperature and humidity variations, reducing the risk of the shower module becoming leaky during use. The potentially toxic shower vapors therefore remain well confined in the shower compartment 102.

In an embodiment, the doors 108, 109, 118 and 119 may be equipped with a return spring guaranteeing its closure each time a victim goes through, again with the aim of avoiding the dispersion of potentially toxic shower vapors towards the outside of the shower module 102, in particular towards the side of the exit chamber 120 whose cleanliness and harmlessness must be preserved.

The doors 108, 109, 118 and 119 may also be equipped with an oculus of dimensions equal to 120×120 mm, for example, especially on the entrance side (right side of unit 100). These oculi can be located approximately 1500 mm from the floor of the shower module 102. Thus arranged, they allow a person located outside the shower module 102 on the steps presented in the foregoing, including the next persons in each decontamination line L1 and L2, to check what is happening in the shower compartments in order to, for example, anticipate their entry into said shower module.

Each of the shower compartments of the shower module 102 comprises two shower areas adjacent to each other in the transverse direction Y of the unit 100. Each zone therefore has dimensions of approximately 1000×900 mm, i.e. 1000 mm long (in the transverse direction Y) by 900 mm wide (in the longitudinal direction X). Each area is equipped with a shower head. The first one, for the shower compartment area on the entrance side (left side in the example considered here) has, in the figures of the attached drawings, the reference 134 for the line L1 and the reference 135 for the line L2. The second one, for the shower compartment area on the exit side (right side of the truck 200 in the example considered here), is marked 136 for line L1 and 137 for line L2. The height from the floor of the shower module 102 to each shower head 134, 135, 136 and 137 is approximately 2000 mm.

The water supply to said first shower heads 134 and 135 and to said second shower heads 136 and 137 is through two respective circuits, which are independent of each other. A first circuit for washing (decontamination) feeds the showers 134 and 135, and a second circuit for rinsing feeds the showers 136 and 137. The first circuit is connected to a mixing pump to add a washing agent to the water. The second circuit for rinsing is supplied with clean water.

Figure 6:
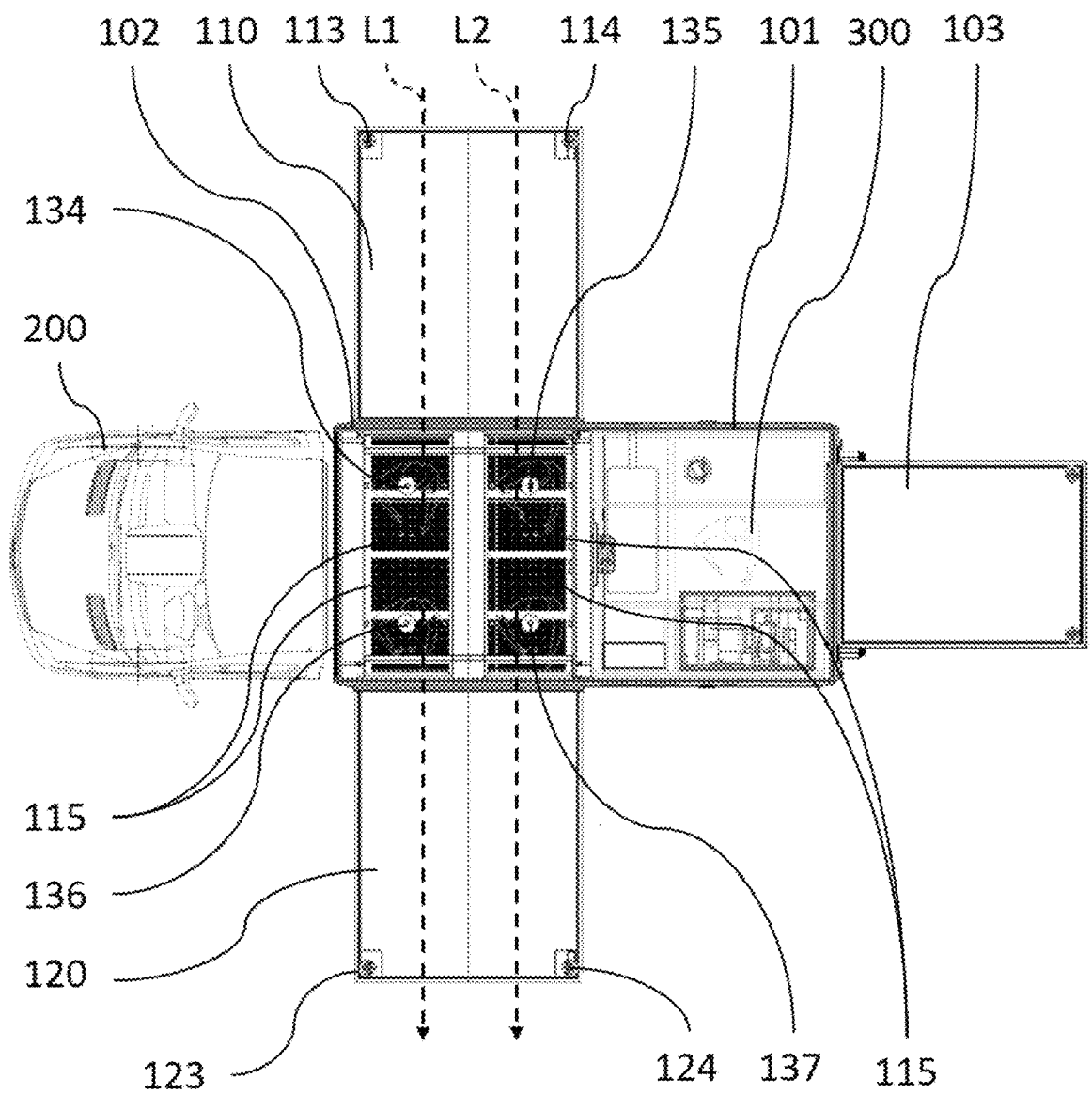
FIG. 6 is a top view of the able-bodied person decontamination unit of FIGS. 2 and 3.

In the example of an able-bodied shower module with two parallel lines L1 and L2 which is shown in particular in FIG. 6, the shower module can accommodate four people simultaneously, one person under each of the showers 134, 135, 136 and 137, respectively. Preferably, however, each shower compartment respectively associated with one of the decontamination lines L1 and L2 (and which includes the area under the washing shower 134 or 135, respectively, as well as the area under the rinsing shower 136 or 137, respectively) accommodates only one person at a time. The person first moves to the area under the washing shower and receives a washing shower there, before moving to the area under the rinsing shower and receiving a rinsing shower there.

In all cases, and as shown in FIG. 6, two people travel in parallel to each other, within line L1 and line L2, respectively. At the same time, two other people are walking behind these two people, respectively. Likewise, two other people precede them in these two lines, respectively An air extractor equipped with a Very High Efficiency (VHE) filter may be arranged above the showers, in particular in order to prevent the air in the decontamination zone comprising the washing showers 134 and 135 (on the side of the entrance to the shower module 102, on the right of the vehicle 200) from polluting the air in the rinsing zone comprising the rinsing showers 136 and 137 (on the side of the exit from the shower module 102, on the left of the vehicle 200). The suction flow rate is for example 3000 m³/h. The clogging of the filter can be checked by a suitable pressure gauge to measure the vacuum upstream of the filter.

Within the shower module 102, the shower compartments respectively associated with the two decontamination lines L1 and L2 may be separated from each other by a canvas wall, for example of PVC canvas having a density of 500 g/m². This wall can be removable, so that when it is removed, a mother and child can pass together at the same time, for example. The installation or removal of such a movable canvas wall takes very little time.

The walls and ceiling of the shower module 102 can be made of a sandwich panel whose facings are made of non-porous polyester, preferably completely smooth and therefore easily decontaminable.

The floor of the shower module 102 can be made of rigid gratings 115, for example made of stainless steel, placed on crosspieces also made of stainless steel, which makes it easily removable. Removal of the gratings also allows access to one or more wastewater collection buffer tanks disposed below, for decontamination after the decontamination cell 100 is no longer in use. The gratings 115 are preferably non-slip to prevent the risk of people slipping and falling in the shower module.

In embodiments, the shower module advantageously comprises a single buffer tank placed under the showers, which allows the wastewater from the four showers 134-137, to be collected and directed to the wastewater collection pump. To this end, the wastewater collection reservoir has a slope to a suction area for a wastewater pump, detailed further, infra.

Given the height of the cell 100 from the ground when mounted on the chassis of the carrier truck 200, the shower module 102 can be raised and lowered by steps that are provided for accessing and exiting said shower compartment. These steps may be separate components of the shower module 102, or they may be retractable components from ad-hoc housings provided in the chassis of the carrier truck 200, for example.

With particular reference to FIGS. 7 and 8, there are thus two steps 201 and 202 on the right side, one for each decontamination line L1 and L2, respectively, provided for entry (ascending) into the respective shower compartment of the shower module 102. And there are likewise two steps 211 and 212 on the left side, one for each decontamination line L1 and L2, respectively, provided for the exit (descending) from the respective shower compartment of the shower module 102. Ideally, and especially considering the wet environment, especially on the descent side that follows the showering operation of the persons, i.e. on the left side of the cell 100 in the example, the steps are preferably non-slip.

Advantageously, the entry and exit of the persons is via an entrance chamber and/or via an exit chamber which are adjacent to the shower module 102 in the transverse direction Y, to the right and to the left of the unit 100, respectively. These chambers can be realized as transverse extensions 110 and 120 of the shower module. Advantageously, these extensions are installed on-site only, when the carrier truck 200 is stationary and is stabilized by jacks, for example.

Preferably, these extensions 110 and 120 are integral with the cell 100, and are retracted into or against the side walls of said cell.

The unit 100 thus comprises a first retractable extension of the shower module 102 in the direction of the transverse axis, on one side of said shower module. In the example shown in the figures and in particular in FIG. 4, this extension 110 is located on the right side of the module 102. It serves as an entrance chamber for people to access the shower module 102. From a usage standpoint, the extension 110 is adapted to provide a compartment for people to undress before they enter the shower module. More particularly, in the extension 110 there is one such compartment for each of the decontamination lines provided by the decontamination unit 100. It is known that the removal of the contaminated persons' clothes alone represents removing more than 80% of the contaminants. Contaminated clothing, for example, is deposited in baskets (not shown) which are placed on the floor or hung in the entrance chamber 110, for removal and destruction, in most cases in which the decontamination unit 100 is being used.

As a reminder, in the example of an able-bodied person decontamination unit shown in FIGS. 2, 3, 6, 7 and 8, the unit comprises two decontamination lines L1 and L2, which are adapted to be operated in parallel to each other. These lines L1 and L2 run parallel to each other in the transverse direction Y. The extension 110 thus comprises two undressing compartments, namely one such compartment for each of the decontamination lines L1 and L2, respectively.

Figure 4:
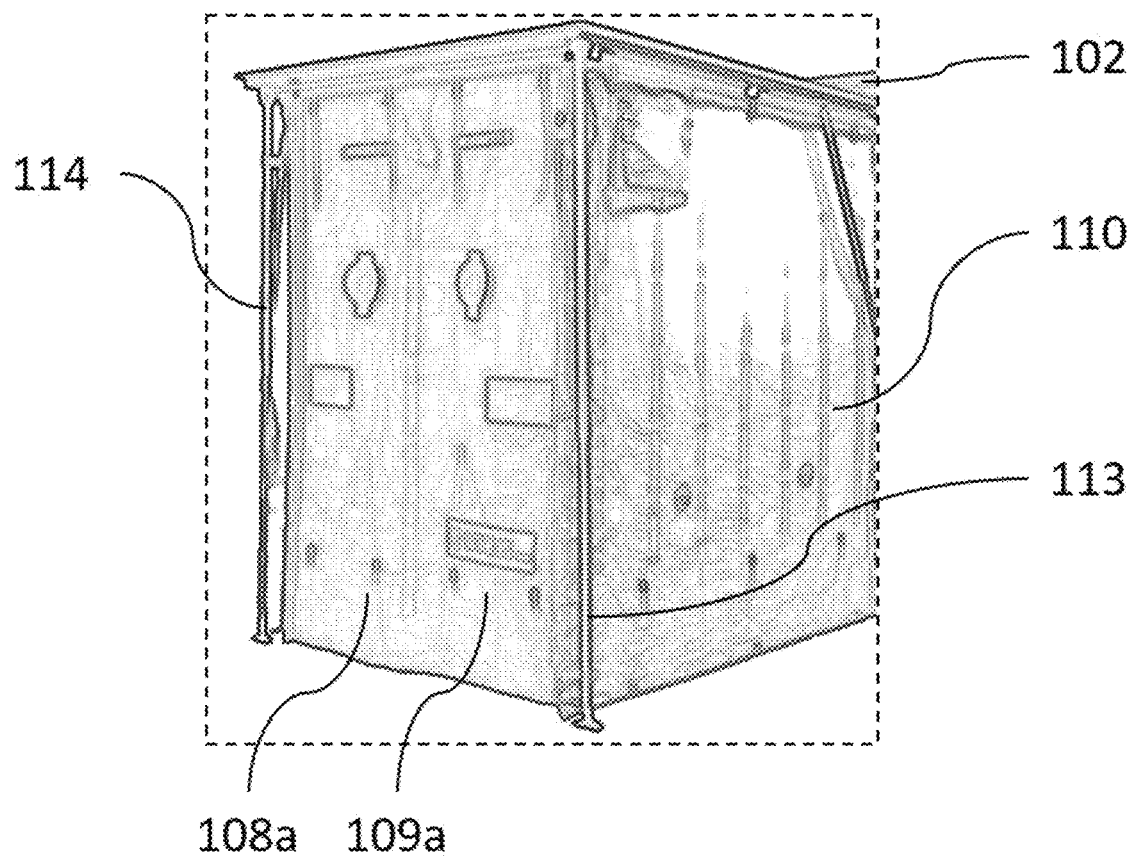
FIG. 4 is a three-dimensional view of a side extension of the shower module of the shower unit of FIGS. 2 and 3, forming an entrance chamber for the undressing of persons.

Access to each undressing compartment is through a door which, in FIG. 4, is referenced 108a for line L1 and 108b for line L2, respectively. Each door can be equipped with zippers, and can be held in an upright position.

The dimensions of each compartment respectively associated with line L1 and line L2 in the extension 110 forming the entrance chamber are, for example, equal to 2000×900 mm, i.e. 2000 mm long in the transverse direction Y, and 900 mm wide in the longitudinal direction X.

Alternatively or additionally, the unit 100 according to embodiments may comprise a second retractable extension of the shower module 102 in said transverse Y axis direction, on the other side of said shower module. In the example shown, this extension 120 is located on the left side of the module 102. It serves as an exit chamber for the exit of persons from the shower module 102. From a usage standpoint, the extension 120 is adapted to provide a compartment for people to dry off and get dressed again after they leave the shower module 102, which has a wet environment.

Figure 5:
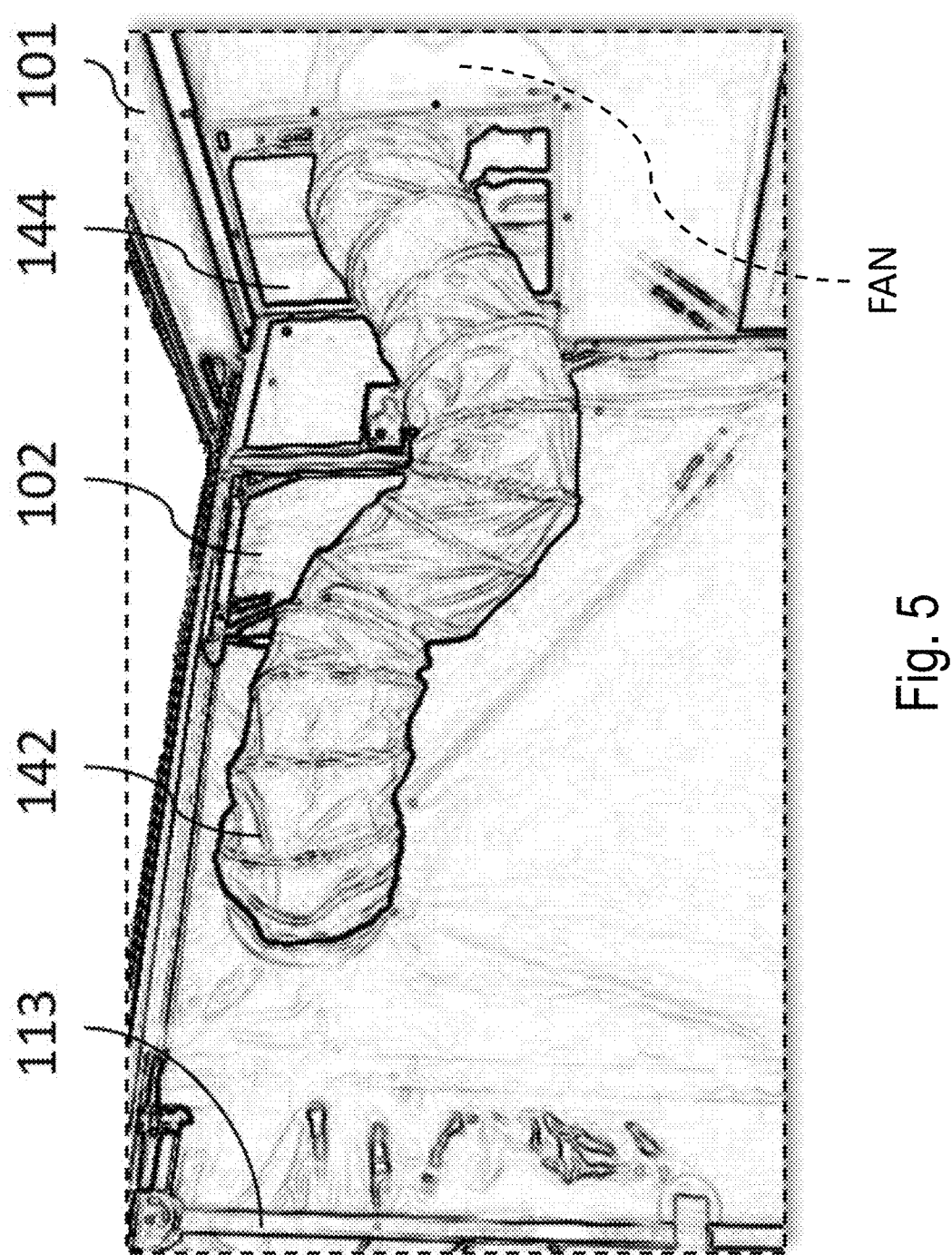
FIG. 5 is a partial three-dimensional view of a further side extension of the shower module of the shower unit of FIGS. 2 and 3, forming an exit chamber for the drying/re-dressing of persons, showing an air diffusion duct opening into the exit chamber.

In an embodiment illustrated in FIG. 5, the technical module 101 comprises a fan for providing an air flow, for example 1500 m³/h, which is connected to an air diffusion duct 142 opening into the dressing chamber 120. This air flow ensures an overpressure sweep of air from the exit to the entrance of the mobile decontamination unit. The potentially contaminated air is therefore returned from the exit to the entrance of the decontamination line in question, i.e. in the opposite direction to the direction of movement of people along decontamination lines L1 and L2. This avoids, or at least greatly reduces, the risk of dispersal of contaminants along the decontamination lines, particularly when opening the rigid doors 108, 109 and 118,119 of the shower module 102 which could otherwise generate a contaminated air stream along the lines L1 and L2 through the shower module. In one embodiment, the technical module 101 comprises a housing 144 closed by a hatch, wherein the air diffusion duct 142 is folded and stored when the decontamination unit is not in use.

The re-dressing chamber 120 can be equipped, inside, with straps allowing the storage of single-use clothes, which the persons put on after their decontamination in order to be able to go home.

Similarly to the extension 110 forming the entrance chamber 110, in the extension 120 forming the exit chamber there is such a re-dressing compartment for each of the decontamination lines L1 and L2 provided by the decontamination unit 100.

The exit from each re-dressing compartment is through a door which, in FIG. 3, is referenced 118*a* for line L1 and 119*a* for line L2, respectively. Each door can be equipped with zippers, and can be held in an upright position.

As for the extension 110 forming the entrance chamber, the dimensions of each compartment respectively associated with line L1 and line L2 in the extension 120 forming the exit chamber are, for example, equal to 2000×900 mm, i.e. 2000 mm long in the transverse direction Y, and 900 mm wide in the longitudinal direction X.

In embodiments, the extensions 110 and 120 of the cell 100 may be formed of canvases, for example PVC canvases having a density of 500 g/m$^2$. The materials from which they are made can be fireproofed, with a M2 classification (hardly flammable) to the classification defined in the series of French standards NF P92-5XX (for example, standard NF P92-507), for safe use on sites hit by, or subject to, a fire risk.

In embodiments, when the decontamination cell 100 is not in use, the canvases remain permanently folded in boxes located at the top of the shower module 102, on each of the right and left sides for the extensions 110 and 120, respectively. This allows the decontamination unit to be set up quickly by simply unfolding the extensions. The estimated start-up time of the decontamination unit is less than 15 minutes, with two operators.

In use, the unfolded extensions 110 and 120 of the cell 100 can be held in place by poles that hold the extension together with its canvases. These posts 113 and 114 for the extension 110, and 123 and 124 for the extension 120, may for example be made of stainless steel. Stainless steel is an inert material that is easy to decontaminate. The outer canvases are designed to be able to hook onto the poles 113,114 and 123,124 via a VELCRO® strip system so that the canvas walls of the extensions 110 and 120 remain vertical during use of the mobile unit 100. In the folded configuration of the extensions 110 and 120, the posts 113,114 and 123, 124 respectively, are folded and integrated into the corresponding extension.

The canvases are attached to the extension. To deploy them, simply open the extension, unroll the outer canvases and connect them at the corners with a VELCRO® system. Advantageously, the canvases may be marked "Entrance" or "Exit" for the extensions on each right or left side, respectively, of the cell 100.

In summary, each of the decontamination lines L1 and L2 of the decontamination unit 100 comprises, for the decontamination of a person, four stages or stations through which the person successively passes, namely:

the undressing compartment in the entrance chamber 110;
the washing shower area in the first part of the shower module (on the side of the entrance 108 or 109);
the rinsing shower area in the second part of the shower module (on the exit side 118 or 119); and,
the drying and re-dressing compartment in the exit chamber 120.

At each of the above stations, the person is the object and/or performer of a respective step of a cell implementation method which comprises four successive steps for the wet decontamination of a person. These steps are, in this order, the undressing, the washing shower, the rinsing shower, and the drying and dressing of the person.

At each of the above-mentioned positions and for the performance of each of the above steps, the person is alone in an enclosed space and out of sight of other people. In other words, that person is isolated from the other persons forming a group of persons to be decontaminated since, for each of the lines L1 and L2, only one person at a time is in the undressing compartment of the entrance chamber 110, in the shower compartment of the shower module 102, and in the drying/re-dressing compartment of the exit chamber 120.

This is advantageous from a health perspective. It reduces the risk of cross-contamination between people in the decontamination unit, where spaces are narrow and people are very close to each other.

It is also an advantage from the standpoint of respecting the privacy of the persons, which is indirectly favorable to the speed of the process of decontaminating a person, and thus to the performance of the decontamination unit in terms of the flow of the persons to be decontaminated. Indeed, from the undressing compartment (including) in the entrance chamber 110, to the re-dressing compartment (including) in the exit chamber 120, each person is isolated from the other persons to be decontaminated. Thus, there are no modesty issues affecting their behavior that could potentially hinder their progress along the decontamination line. People feel respected, and therefore cooperate all the more willingly.

The advantages mentioned above also result from the fact that the undressing compartment and the drying/re-dressing compartment are adjacent to the shower module 102. People do not have to travel through an empty space between the two compartments. They are isolated from other people both from a health perspective and from the human and/or ethical perspective (respect for the human body, social codes, morals, etc.).

Nevertheless, the fact that one person may be showering in the shower module 102 while the next person is already getting ready by undressing in the entrance chamber 110, and while the previous person is completing the decontamination process on their own body by getting dressed in the exit chamber 120, is conducive to a high flow rate of decontaminated people. Of course, the design of the decontamination lines according to the proposed embodiments allows for the parallel arrangement of several decontamination lines such as lines L1 and L2. The more decontamination lines there are, the greater the throughput. As the control module is common to all decontamination lines, the cost of adding a decontamination line is marginal. The upper limit results from the limited consumable resources (electrical energy, clean water) in the context of a mobile decontamination unit. This can be a limiting constraint if the mobile unit does not have access to an electrical and/or water supply network at the site of the intervention, or to easily renewed resources.

In the example shown in FIGS. 2, 36, 7 and 8, the two decontamination lines L1 and L2 are adjacent to each other in order to optimize the space available in the shower module and its extensions 110 and 120. The two decontamination lines L1 and L2 can be physically separated from each other by canvas walls, for example, PVC canvas with a density of 500 g/m$^2$. Such a material offers the advantage of being easily cleanable, so that it can be reused. Also, it is an inexpensive material, so that canvas walls can advantageously be single-use. With opaque screens, a visual isolation is achieved between the two lines L1 and L2, which means that a person in line L1 cannot see or be seen by another person in the same level in line L2. The canvases for the internal separation of the respective compartments in the undressing chamber 110 and in the re-dressing chamber 120 can be suspended from the canvas ceiling and rolled up before the respective extension is folded. Thus, when cell 100 is placed in service, this partition unwinds and is put in place by gravity alone. This contributes to the ease and speed of beginning service.

The aforementioned contiguity between decontamination lines L1 and L2 is not mandatory. The two decontamination lines can be spaced apart, for example, to better isolate them from each other from a health perspective, reducing the risk of possible cross-contamination. Another reason and advantage of such a spacing in the direction of the longitudinal axis X between lines L1 and L2 may be to allow for the observance of rules of propriety applying to the population of persons to be decontaminated. This can also help to better respect the modesty and privacy of the persons to be decontaminated.

Comparable or similar results can be obtained for the entrance chamber 110 and for the exit chamber 120 with hard partition walls, arranged between the different compartments of the two decontamination lines L1 and L2. These can be partitions made of sandwich panels whose facings, i.e. the external surfaces, can be made of non-porous polyester, ideally completely smooth, in order to be easily decontaminated.

In order to provide illumination of the working area outside and around the decontamination unit each side face as well as on the rear face of the cell 100 may comprise lights, for example LED lights. These LED lights can be integrated into the upper crossbar of the cell, and in particular of the technical module 101. They make it possible to illuminate the working area around the decontamination cell at night. They may be controlled by a general control panel 109 of the technical module 101 of the cell 100, accessible from the outside, for example on the left side of the cell 100 as shown in FIG. 3. The fact that this general control panel 109 is accessible from outside the cell 100 allows the external lighting to be put into service as soon as the intervention area is reached, in order to facilitate the setting up of the unit at night. This general control panel 109 may also be used to control the installation of the stabilizing jacks of the carrier chassis of the carrier truck 200 prior to the deployment of the side extensions 110 and 120 of the shower module 102. If such deployment is, in whole or in part, electrically controlled, then such control may advantageously also be controlled by the operator via the general control panel 109.

The interior lighting of the shower module 102 and, if applicable, of its extensions 110 and 120, can be achieved by lights (again of the LED type, for example) placed in each compartment, either inside the shower module 102 for the lighting of the shower compartments, or outside on the external walls of said module 102 for the lighting of the lateral extensions 110 and 120. The dimensions of the interior lighting are designed to provide optimum working comfort without creating shadows. The lights that provide interior lighting may be controlled by an electrical cabinet (not referenced in the figures) associated with a control panel, which are included in the technical module 101 of the cell 100.

The shower module 102 may include a light indicator, such as a two-color red/green indicator, at each of the entry doors 108 and 109 outside the module 102, and at each of the exit doors 118 and 119 inside the module 102, to show individuals when to enter, or exit, the shower module, respectively. Other indicator lights, including dual-colored red/green or other indicators, may also be mounted between the two showers 134 and 136, or 135 and 137 of each of the shower compartments of the L1 decontamination line and the L2 decontamination line, respectively. This allows the flow of people in these decontamination lines to be more fluid, thus increasing the throughput of each decontamination line. Thanks to the light indicators, each person knows when they must progress along the decontamination line. The above light indicators can be controlled by the electrical cabinet associated with the control panel, which are included in the technical module 101 of the cell 100.

The electrical cabinet and the control panel are located in the technical module 101 of the cell 100. They include all the controls for operating all the equipment necessary for the proper functioning of the decontamination cell 100, and in particular the shower module 102.

The operation of the unit's showers can advantageously be automatic, which favors a greater flow of people being treated. The switching on/off of the showers is handled by the electrical cabinet, which controls the solenoid valves mounted on the piping. These solenoid valves are used to control the flow of water to the gantries that supply the shower heads 134, 135, 136 and 137. However, the two decontamination lines L1 and L2 can be operated independently of each other. Thus, if one line is stopped for any reason, the other can continue to operate. For example, there is one solenoid valve per shower head, which allows each shower to be controlled on/off independently of the others.

Control buttons and indicator lights on the electrical box form a human-machine interface that allows the two decontamination lines to be controlled, either in automatic mode or in manual mode by an operator 300 when positioned in the technical module 101, which the operator accesses through the rear door 103. The setting of the operating time of the showers can be done via a menu displayed on a screen, which is easy to use. At any time during the operation of the decontamination unit 100, the programmed times can be changed under the control of the operator 300. In parallel and in connection with the operation of the showers, the aforementioned light indicators which are placed above the entrance door 108 or 109 (outside the shower module), the exit door 118 or 119 (inside the shower module), and in the middle of the two showers 134 and 136 or the showers 135 and 137, light up in red or green depending on the operation of the showers, in order to allow the persons to be decontaminated to move apace along the decontamination line L1 or L2, respectively, which they follow.

As will be appreciated, in addition to the two persons who may simultaneously be in the shower module 102 as discussed above with reference to FIG. 6, two persons may simultaneously be in the entrance chamber 110 (with one person in the undressing compartment of each decontamination line L1 and L2, respectively), and be in the process of undressing. In addition, two individuals may simultaneously be in the exit chamber 120 (one in the drying and re-dressing compartment of each decontamination line L1 and L2, respectively), and be drying and dressing in the single-use garments they find in that exit chamber 120.

In other words, at each step of the decontamination cycle of a person, which includes four steps (undressing, washing shower, rinsing shower and re-dressing), three people are simultaneously involved in the decontamination operations, for each of the decontamination lines L1 or L2:

a person in entrance chamber 110 undressing;

a person in the shower module 102, under the washing shower 134 or 135, respectively, or subsequently at a forward station in the decontamination line, i.e., under the rinsing shower 136 or 137, respectively; and finally, a person in the exit chamber 120 drying and re-dressing.

With each cycle, and in rhythm with the red/green lighting of the light indicators, the people advance in line L1 or line L2. As the above third person leaves the exit chamber 120 through door 118a or 119a, respectively, and thus leaves the decontamination unit 100, that person is replaced therein by the person leaving the shower module 102 through exit 118 or 119, respectively. The latter person is then replaced in the shower module 102 by the person who was in the undressing compartment of the entrance chamber 110, and who accesses said shower module 102 through door 108 or 109, respectively, while furthermore a new person enters the entrance chamber 110, through door 108a or 109a, respectively, and thus accesses the decontamination unit 100.

As will be understood, the above process is carried out in parallel for the two decontamination lines L1 and L2, in the two respective shower compartments of the shower module 102, in the two respective undressing compartments of its extension 110 and in the two respective drying/undressing compartments of the extension 120. Advantageously, the two decontamination lines L1 and L2 are operated in parallel with common technical means that are present in the technical module 101.

In addition to or instead of the L1 and L2 decontamination lines of the shower module for able-bodied victims (AB) that have been presented so far, a shower module may include an L3 decontamination line for disabled victims (SD).

Figure 9:
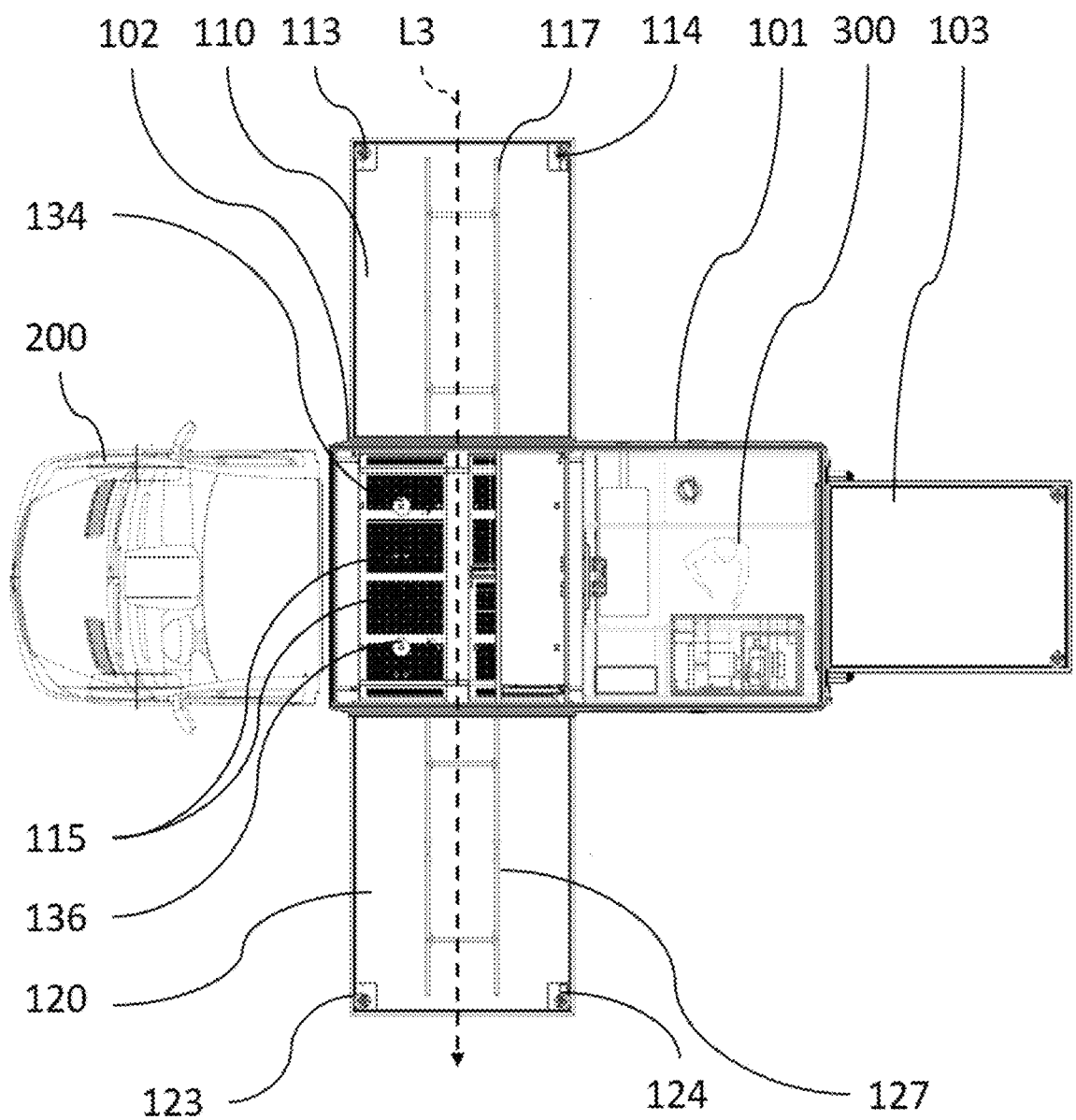
FIG. 9 is a top view of a decontamination unit equipped with a shower module for disabled persons of FIGS. 2 and 3.

A shower module 102 with such a decontamination line L3 will now be described with reference to FIGS. 9, 10 and 11. As will be appreciated, this decontamination line L3 is capable of being operated, in a fallback mode, as a decontamination line for able-bodied persons with the technical means present in the technical module 101.

Overall, the design of the disabled victim shower module is identical to that of the able-bodied victim shower module, except for the detail of the decontamination lines.

In the case of the disabled persons' shower module, the space used to create the two disabled person lines L1 and L2 of the shower module 101 and its side extensions 110 and 120, is used to create only one decontamination line L3 which is suitable for wet decontamination of disabled persons. The module further comprises some additional equipment specific to the decontamination line L3 for disabled persons.

Thus, entra with stretcher rails 117 and 127 are arranged in the entrance chamber 110 and in the exit chamber 120, respectively. This equipment is made, for example, of stainless steel. The shower compartment 102 is equipped with a buff with two positions, low and high, also made of stainless steel, driven by a hydraulic unit that feeds a double-acting cylinder, or a manual pump in fallback mode. The low position of the lifting table is flush with the stretcher rails 117 of the entrance chamber 110 and the stretcher rails of the exit chamber 120. The elevator base comes into operative alignment with said stretcher rails 117 and 127. These three groups of stretcher elements form a stretcher line in the direction of the transverse axis Y.

Preferably, the decontamination unit is provided with three stretchers equipped with wheels, allowing a disabled victim to pass through the different compartments of the unit without needing to be carried: the undressing compartment in the entrance chamber 110, the shower compartment in the shower module 102, and the drying/re-dressing compartment in the exit chamber 120.

The lifting table in the shower module 102 is provided with four inclined sides, one at each end of the two rails thereof for receiving the stretcher. These inclined sides have a stop zone allowing the stretcher to be stopped in translation. When a stretcher with a disabled victim on it has been brought into position on the lifting table and immobilized in translation by the wheels mating against the stop of the inclined sides, the table is raised to its high position. Thus, the victim is at a height to receive a shower by an operator.

On the water supply circuit of the washing and rinsing gantries, there is a tap equipped with a ¼T valve and a quick coupling. This allows the connection of two hand showers for the decontamination of disabled victims. Advantageously, the stretcher canvas can be perforated so that water can flow through.

Figure 10:
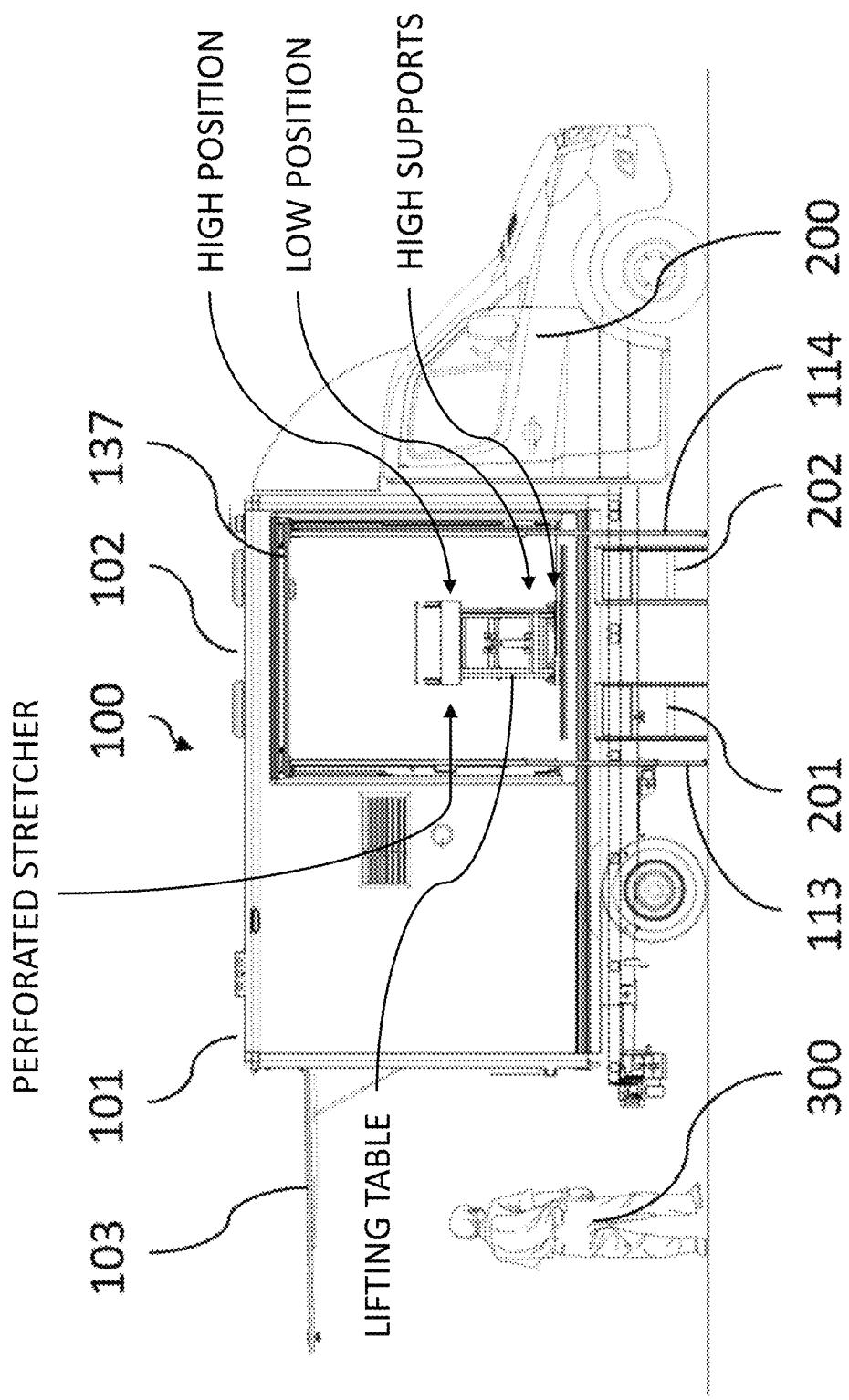
FIG. 10 is a right side view of the disabled person decontamination unit of FIG. 9.
Figure 11:
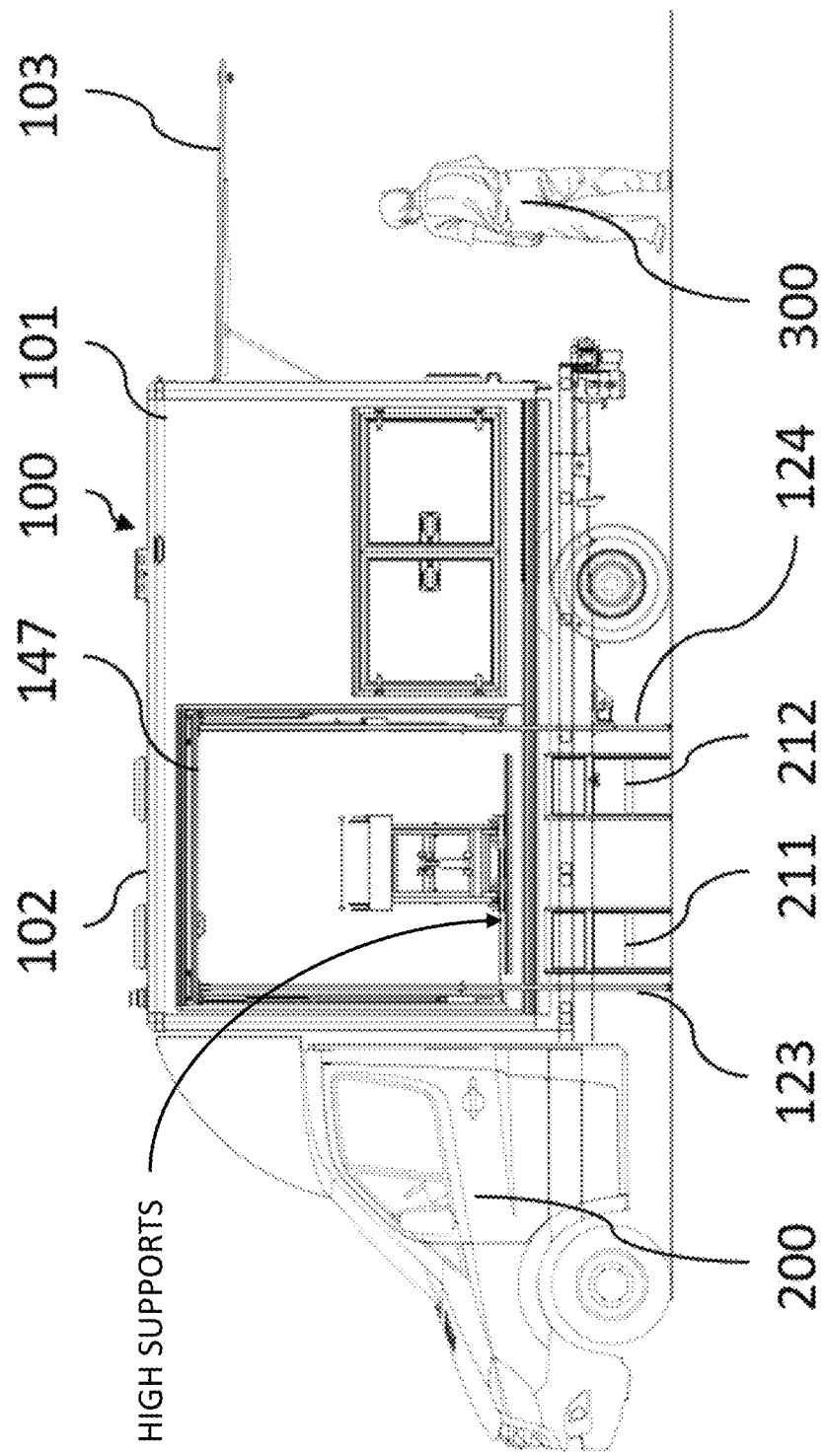
FIG. 11 is a left side view of the disabled person decontamination unit of FIG. 9.

With further reference to FIGS. 10 and 11, access to and egress from the shower module 102 is via flexible curtains 137 and 147 on the right side (entrance chamber side 110) and left side (exit chamber side 120), respectively. These flexible curtains 137 and 147 are for example made of PVC. These curtains can be equipped with a window on each side. The central part of the curtain can be raised when the victim enters or leaves the shower compartment.

The entrance to the undressing compartment and the exit from the re-dressing compartment are both through a door placed at the ends of the extensions. Preferably the door is the full width of the extension, 1800 mm in the example, to facilitate the passage of the stretcher. The door is closed by means of zippers. It can be held in a high position, or at the height of the rails 107 and 117 of the stretcher supports.

Advantageously, the shower module 102 for disabled victims can be used in a fallback mode for a single line of decontamination of able-bodied victims. It is the presence of the lifting table that prevents it from being used for two parallel able-bodied victim decontamination lines. In fact, the lifting table is mounted on a slide and is stored against the front wall of the shower module 102, on the driver's side of the vehicle 200.

The decontamination unit is autonomous in its operation. To this end, it includes a generator which provides the electrical energy necessary for the operation of the various equipment. It also includes a clean water tank for supplying showers, and at least one wastewater recovery tank.

With further reference to FIG. 2 and FIG. 3, in particular, the generator 105 may be placed on the side of the technical module 101, namely the left side in the example shown. It remains permanently installed during the operation of the unit. It is supplied with fuel from a common diesel tank (not shown), for example with a capacity of 100 liters, of the technical module 101.

This could be, for example, an EPS6000DE HA/LS generator. Such a generator offers a maximum power of 5.5 kV, with a continuous power of 5 KVA, equipped with a 230V-22A plug. The alternator is a SINCRO® EK2MCT EK6 6 KVA SAEJ609B alternator, delivering a current with a frequency of 60 Hz. The engine is a HATZ 1B40, 1-cylinder, 462 $cm^3$, 3000 rpm, air-cooled.

The person skilled in the art will understand that the above generator is only an example, and that in practice the generator used must be chosen according to the technical characteristics of the application envisaged. Preferably, a power reserve of at least 30% is available, in order to be able to connect ancillary equipment useful for the operation of the decontamination unit, if necessary.

The connection of the generator to the cell is done through a socket placed in the technical room. This allows the cell to be connected to an external 220V/60 Hz electrical distribution network in parking mode, instead of the generator, whenever possible. The generator is then used as a source of emergency power, to ensure operational continuity even in the event of a temporary interruption of the power supply by an electrical distribution network.

For the recovery of contaminated wastewater, the mobile decontamination unit 100 includes one or more ancillary flexible reservoirs, such as the reservoir 420 shown in FIG. 3.

Figure 12:
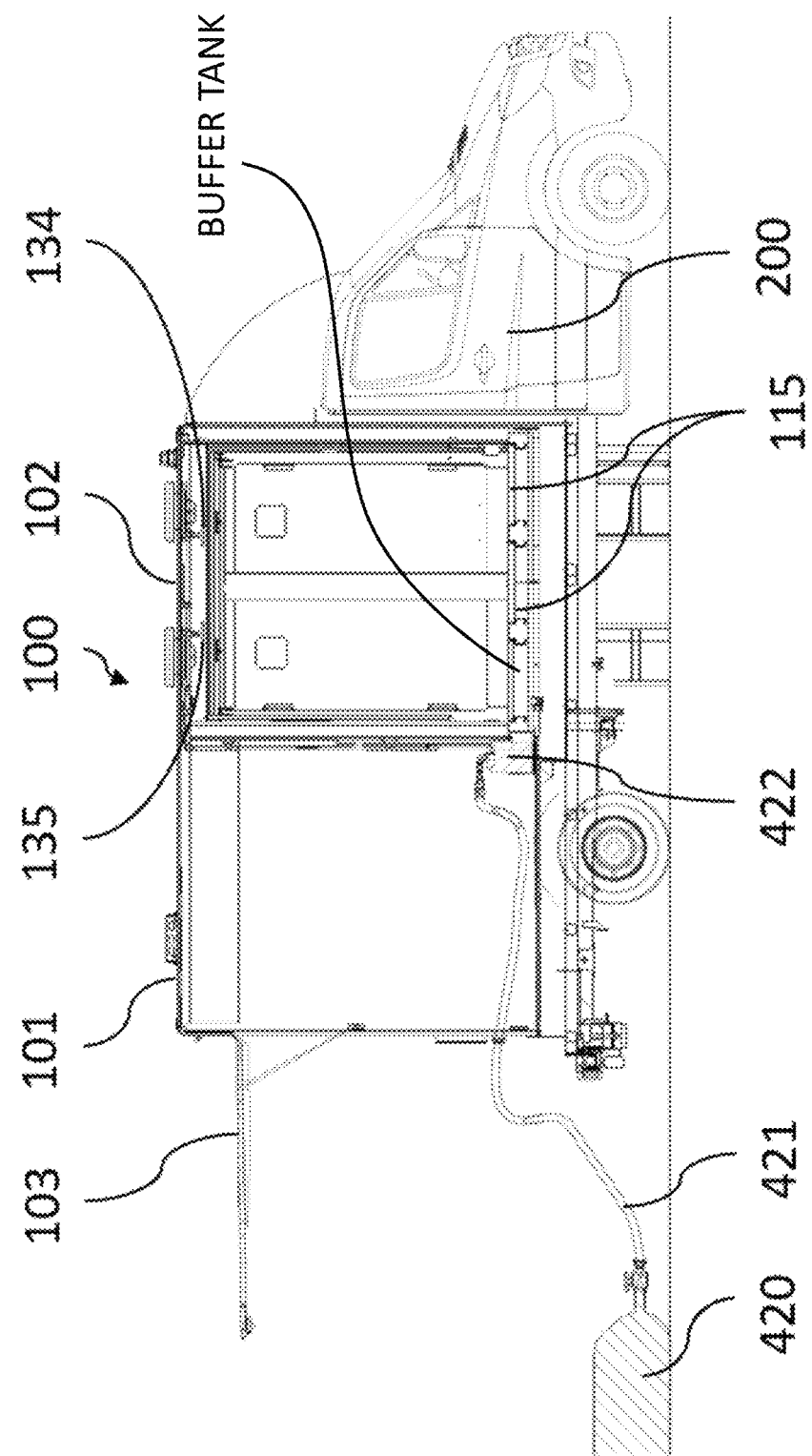
FIG. 12 is a side view of the decontamination unit showing means of discharging the waste water.

With reference to FIG. 12, the buffer tray that is placed under the grated floor 115 of the shower module 102, may comprise a V-shaped profile with a slope directed towards the technical module 101. The latter includes a pump 422, for example a "mop" pump (i.e., a submersible pump that can be placed on the surface to be vacuumed) as shown in FIG. 13, which is adapted and arranged to draw wastewater into the buffer tank. The wastewater is discharged to the flexible recovery reservoir 420 via a flexible pipe 421.

The flexible reservoir(s) is (are) put in place by the operator 300 when the decontamination unit is being installed and placed in service. The flexible reservoir is replaced by another one each time it is full. Being located outside the decontamination unit 100, preferably at the rear of the unit, this replacement operation is easy as is the removal of the full reservoirs. Most importantly, these operations do not interfere with the flow of persons through the shower module 102.

In one example, the mobile decontamination unit is equipped with two flexible tanks of 3000 liters each, made of polyester canvas coated with PVC on both sides, with a density of 1100 g/m². They can be equipped with polypropylene flanges and stainless steel screws. For connection to the 421 hose line, the tanks are equipped with, for example, a ¼T valve and a DN45 fireman's connection.

The pump 422 is electrically powered by a Start/Stop button on the general control panel, it starts automatically when there is water in the buffer tank and stops when there is no more water in it. Forced operation can be carried out to empty the entire buffer tank.

The flow rate of the pump used is 6 m³/h. The particle size of the solid particles that can be sucked in is 6 mm. Preferably, the flow rate of the pump is large enough to ensure that the water in the showers cannot overflow the buffer tank when the decontamination unit is operating at full load.

In an example corresponding to FIG. 13, the submersible pump is powered by 230 V-50 Hz, with a power of 0.4 KW. Its maximum flow rate is 10 m³/h. The pump is able to suck water from 1 mm height. Its electrical power is 480 W.

In embodiments, the supply of clean water to the decontamination cell 100 may be from an external tank 410 included in the trailer that has already been shown above with reference to FIG. 3 to which reference is again made here.

This tank makes it possible to store and transport the water necessary for the operation of the decontamination cell on any intervention site. Advantageously, it can be replaced, when empty, by another comparable tank which can be brought to the site by another vehicle. This can be done without having to move the decontamination unit, and therefore without interrupting its operation.

As shown in FIG. 14, the tank is preferably compartmentalized to reduce the unbalance during movement. Its capacity can be 1000 liters, for example, which gives the decontamination unit a water autonomy of about 6 hours.

The trailer may be equipped with a transfer pump 412 suitable for transferring water to the decontamination cell shower supply circuits. The pump 412 may be electrically powered by the generator of the technical module 101, using a power supply cable associated with said technical module. Alternatively, the pump may be included in the technical module 101.

Figure 15:
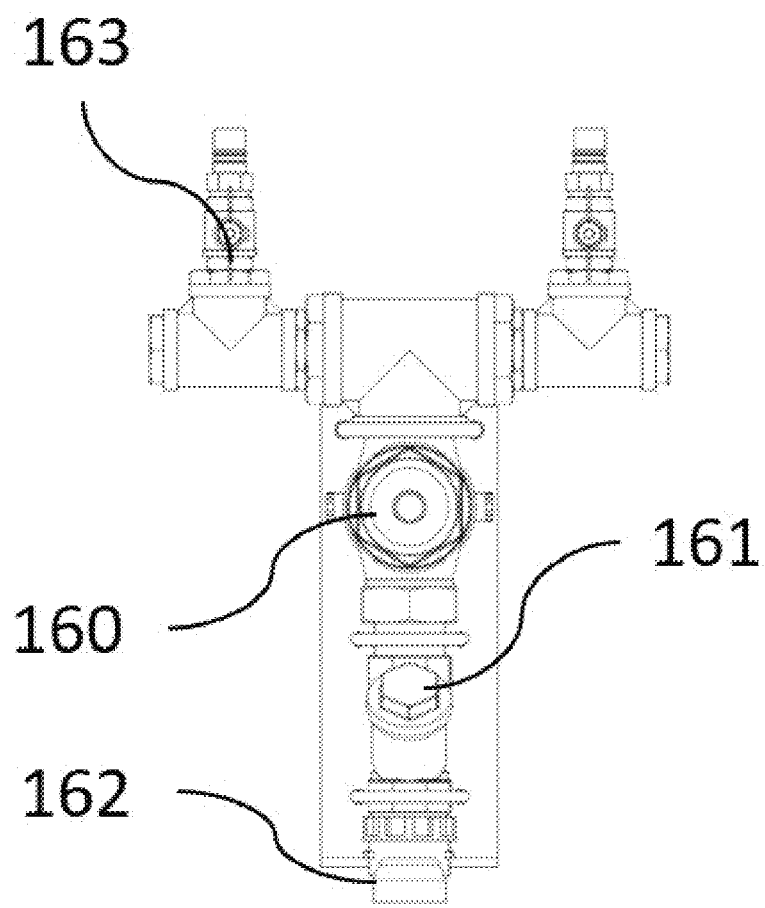
FIG. 15 is a representation of part of the water supply means for the showers of the decontamination unit; and, FIG. 16 is a representation of an element of the water supply circuit of the decontamination unit.

With reference to FIG. 15, the water supply system of the mobile decontamination unit further comprises a water pressure regulator 160. The regulator can be adapted to regulate the water pressure in the supply system to an adjustable value between 0 and 6 bar, for example.

The water pressure regulator 160 can be equipped with a sludge filter 161, and a 0/10 bar steel direct-reading pressure gauge (not shown). For example, the sludge filter 161 can be adapted to filter out all impurities in the water with a diameter greater than 500 microns.

The water pressure regulator 160 can be equipped with a connection 162 at the inlet, for example a DN45 fire-hose connection, for connection to a fire engine, hydrant, or local water network. Thus, the water autonomy of the decontamination unit is no longer limited to the capacity of the tank, as long as another water supply source is available nearby.

In addition, it can be equipped at the outlet with a quarter-turn valve (¼ T) 163 allowing the water supply to the decontamination unit to be shut off at any time.

Figure 16:
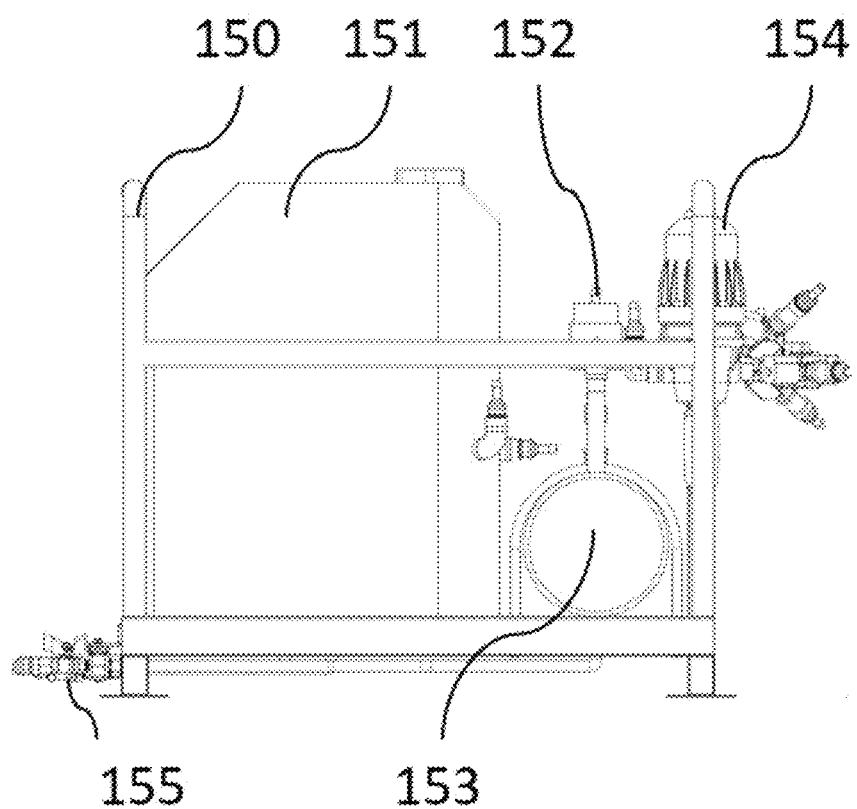

With reference to FIG. 16, the water supply system of the mobile decontamination unit 100 provides a mixed water supply to all showers. It consists of various materials installed in the technical module. Such equipment can be mounted on a tubular frame 150, for example one made of stainless steel, which is secured in the technical module and remains there during the operation of the mobile decontamination unit.

The components of the water supply system are as follows:

an instantaneous boiler 151, having for example a power of 57Kw and a flow rate of 35 L/min running on diesel, the exhaust gases being evacuated to the roof of the technical module. It can be supplied with diesel via a flexible pipe connected to a central tank, for example with a capacity of 100 liters, which is located in the technical module;

a temperature mixing valve 152, allowing the water temperature to be set within a range of 15° C. to 50° C. The temperature is set, for example, by means of a direct-reading graduated wheel. The maximum hot water temperature is, for example, 85° C.;

a buffer tank 153, for example with a capacity of about 20 liters, made for example of stainless steel, and which makes it possible to ensure a homogeneous temperature over the four showers of the shower module envisaged in the present description and as described above;

a mixing pump 154, for example, a proportional flow pump with a control range of 0.2 to 2%, at an adjustable pressure of 0.5 to 6 bar. The operational flow rate can be between 10 L/min and 3 m³/h. The recommended operating pressure is between 2 and 4 bar. This pump is suitable for injecting the decontamination solution into the mixed water. The adjustment is made by means of a direct-reading graduated wheel. The components of the mixing pump advantageously allow corrosive products to pass through. For this purpose, the mixer body and bell can be made of PVDF, for example. It can be equipped with a viscous kit allowing decontamination products whose viscosity can go up to 800 cps at 20° C. to pass through; and drain valves 155, arranged at the bottom of the chassis, allowing the draining, in particular, of the boiler heating body 151, of the tank 153, and of the pump 154.

The above equipment provides satisfactory water temperature regulation and stability regardless of variations in pressure (with a maximum of 1.5 bar), temperature at the mixer inlets, and flow rate (within a range of 3 to 42 L/min).

The present invention has been described and illustrated in the present detailed description and in the figures of the attached drawings in possible embodiments. The present invention is not, however, limited to the embodiments shown. Other variants and embodiments may be deduced and implemented by the person skilled in the art from the present description and the attached drawings.

In particular, the person skilled in the art will understand that the number of decontamination lines is not limited to two as in the example considered in the present description. Furthermore, a combination of one or more shower modules for able-bodied persons, such as the module of FIGS. 6, 7 and 8, and one or more shower modules for disabled persons, such as the module of FIGS. 9, 10 and 11, may be provided, the operation of which is ensured by a single technical module, such as the module 101, sized for this purpose.

Also, although the mobile decontamination unit 100 described herein is particularly suitable for permanent installation on the chassis of a carrier vehicle as shown, other applications are possible. Alternatively, the mobile decontamination unit can be supplied in the form of a container or half-container forming a ready-to-use cell that can be deposited by a crane truck that does not remain on the site of intervention. In such a case, it has lifting hooks on the top and/or holes for the forks of a forklift on the bottom. This configuration is suitable for applications in which the decontamination unit operates on a more permanent basis, for example in a construction site, such as an industrial decontamination site.

In this paper, the term "comprise" or "include" does not exclude other elements or steps. A single processor or multiple other units may be used to implement the invention. The different features presented can be advantageously combined. Their presence in different parts does not exclude this possibility. The reference signs should not be understood as limiting the scope of the invention.

The invention claimed is:

1. A mobile decontamination unit for the wet decontamination of persons, having a generally rectangular parallelepiped shape with a longitudinal axis (X) and a transverse axis (Y), comprising:
    a technical module and at least one shower module, which are adjacent to each other in the direction of the longitudinal axis;
    a first extension of the shower module, which can be retracted in the direction of the transverse axis, on one side of the shower module and/or a second extension of the shower module, which can be retracted in the direction of the transverse axis, on the other side of the shower module;
    wherein the first extension and/or the second extension are made of canvas, and are unfoldable and collapsible with frame elements and posts from which the canvas is supported, said canvas, frame elements, and posts being retractable into the wall of the shower module;
    wherein the shower module and the first and/or second extension thereof further comprise one of:
        at least one able-bodied person-decontamination line; and,
        at least one disabled victim decontamination line for the circulation of persons to be decontaminated by showering in the shower module in the direction of the transverse axis.

2. The decontamination unit according to claim 1, wherein the first and second extensions of the shower module form a person undressing compartment and a person re-dressing compartment, respectively.

3. The decontamination unit according to claim 1, wherein the shower module is equipped with a decontamination shower and a rinsing shower for each decontamination line, each comprising a shower head with a supply circuit fed with a decontamination solution and with another supply circuit fed with clear water, respectively.

4. The decontamination unit according to claim 1, comprising a single buffer tank which is located under a grated floor of the shower module, and further comprising a pump which is located in the technical module and is adapted to draw waste water into the buffer tank and discharge it to one or more flexible waste water collection tanks which may be located outside the decontamination unit.

5. The decontamination unit according to claim 1, wherein the technical module comprises a fan connected to an air diffusion duct opening into the second extension, and adapted to provide an air flow ensuring a sweep of overpressure air from the second extension to the first extension through the shower module.

6. The decontamination unit according to claim 1, comprising at least one stretcher for carrying a disabled person along the disabled person decontamination line, said stretcher having a perforated surface.

7. A method of using a decontamination unit according to claim 1, wherein the operation of showers of the shower module is automatic.

8. The decontamination unit according to claim 1, wherein the shower module as well as its first extension and its second extension as configured able-bodied person decontamination line, at least one able-bodied victim decontamination lines each having a decontamination shower and a rinsing shower disposed adjacently along said transverse axis, which at least two able-bodied decontamination lines are adapted to be operated in parallel with common technical means comprised in the technical module.

9. The decontamination unit according to claim 8, wherein said at least two able-bodied victim decontamination lines are adapted to be operated in parallel but independently of each other.

10. The decontamination unit according to claim 8, wherein said shower module comprises a removable wall extending in the direction of the transverse axis thereby forming two shower compartments of said shower module, said shower compartments belonging to the first decontamination line and the second decontamination line, respectively,
    and wherein the first extension and/or the second extension of the shower module each comprise a wall extending in the direction of the transverse axis to separate said extension into two compartments, said compartments belonging to the first decontamination line and to the second decontamination line, respectively.

11. A mobile decontamination unit for the wet decontamination of persons, having a generally rectangular parallelepiped shape with a longitudinal axis (X) and a transverse axis (Y), comprising:

a technical module and at least one shower module, which are adjacent to each other in the direction of the longitudinal axis;

a first extension of the shower module, which can be retracted in the direction of the transverse axis, on one side of the shower module and/or a second extension of the shower module, which can be retracted in the direction of the transverse axis, on the other side of the shower module, wherein the shower module and the first and/or second extension thereof comprise at least one disabled victim decontamination line for the circulation of persons to be decontaminated by showering in the shower module in the direction of the transverse axis;

wherein the first extension and/or the second extension are made of canvas, and are unfoldable and collapsible with frame elements and posts from which the canvas is supported, said canvas, frame elements, and posts being retractable into the wall of the shower module.

12. The decontamination unit according to claim 11, wherein the at least one disabled victim decontamination line, is adapted to be operated, in a fallback mode, as an able-bodied person decontamination line.

13. A mobile decontamination unit for the wet decontamination of persons, comprising:

a carrier vehicle having a chassis with a longitudinal axis (X) and a transverse axis (Y);

a cell mounted on said chassis of said carrier vehicle, said cell comprising:

a technical module arranged within said cell;

a shower module arranged within said cell and adjacent said technical module about said longitudinal axis;

a first extension of said shower module, which can be retracted in the direction about said transverse axis, on a first side of said shower module;

a second extension of said shower module, which can be retracted in a direction about said transverse axis on a second side of said shower module, wherein the shower module and the first and/or second extension thereof may be configured as:

at least one able bodied person-decontamination line for the circulation of persons to be decontaminated by showering in the shower module in the direction of the transverse axis;

wherein the first extension and/or the second extension are made of canvas, and are unfoldable and collapsible with frame elements and posts from which the canvas is supported, said canvas, frame elements, and posts being retractable into the wall of the shower module; and, a disabled bodied person-decontamination line, for the circulation of disabled persons to be decontaminated by showering in the shower module in the direction of the transverse axis.

14. The mobile decontamination unit for the wet decontamination of persons recited in claim 13, wherein said shower module is equipped with a decontamination shower and a rinsing shower for each of said decontamination lines, each comprising a shower head with a supply circuit fed with a decontamination solution and with another supply circuit fed with clear water, respectively.

15. The mobile decontamination unit for the wet decontamination of persons recited in claim 13, wherein the disabled person decontamination line comprises:

high supports with stretcher rails arranged in the first extension and in the second extension; and, a lifting table with a low position and a high position, arranged in the shower module, said low position of the lifting table being flush with the stretcher rails of the first extension and with the stretcher rails of the second extension, the lifting table being operatively aligned with said stretcher rails so as to form a stretcher line in the direction of the transverse axis Y.

* * * * *